(12) United States Patent
Weckwerth et al.

(10) Patent No.: US 6,758,845 B1
(45) Date of Patent: *Jul. 6, 2004

(54) AUTOMATIC FIRING APPARATUS AND METHODS FOR LASER SKIN TREATMENT OVER LARGE AREAS

(75) Inventors: Mark V. Weckwerth, Pleasanton, CA (US); John P. Beale, Fremont, CA (US); James Z. Holtz, Livermore, CA (US); Robert E. Grove, Pleasanton, CA (US)

(73) Assignee: Lumenis Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/415,575

(22) Filed: Oct. 8, 1999

(51) Int. Cl.[7] .............................................. A61B 18/18
(52) U.S. Cl. ............................. 606/9; 606/10; 606/12; 606/13; 607/88; 607/89; 128/898; 356/4.01; 356/444; 356/614
(58) Field of Search .......................... 606/8, 9, 10–12, 606/13; 607/88, 89; 128/898; 356/3.01–3.08, 4.01, 614, 444

(56) References Cited

U.S. PATENT DOCUMENTS

| 5,344,418 A | * | 9/1994 | Ghaffari | 606/9 |
| 5,464,436 A | * | 11/1995 | Smith | 607/89 |
| 5,501,680 A | * | 3/1996 | Kurtz et al. | 606/9 |
| 5,662,643 A | * | 9/1997 | Kung et al. | 606/3 |
| 5,725,522 A | * | 3/1998 | Sinofsky | 606/8 |
| 5,843,072 A | * | 12/1998 | Furumoto et al. | 606/9 |
| 5,879,346 A | * | 3/1999 | Waldman et al. | 606/9 |
| 5,968,033 A | * | 10/1999 | Fuller et al. | 606/9 |
| 6,104,959 A | * | 8/2000 | Spertell | 607/101 |
| 6,171,302 B1 | | 1/2001 | Talpalriu et al. | |

FOREIGN PATENT DOCUMENTS

| WO | WO 98/51235 | 11/1998 |
| WO | WO 99/11324 | 3/1999 |

* cited by examiner

Primary Examiner—Roy D. Gibson
Assistant Examiner—Ahmed Farah
(74) Attorney, Agent, or Firm—Eitan, Pearl, Latzer & Cohen Zedek, LLP

(57) ABSTRACT

Laser skin treatment apparatus includes a handpiece for delivering laser-radiation pulses from a laser to an area of skin being treated. The area being treated is larger than an area treatable in a single firing of the laser. The larger area is treated by treating adjoining sub-areas within the larger area by repeated firings of the laser. The laser is fired automatically depending on the position of the handpiece in the larger area. Several arrangements for determining the position of the handpiece are disclosed. These include optical detection by the handpiece of indicia drawn on the skin being treated; optical, magnetic, or mechanical detection of indicia on a separate guide for the handpiece or on a roller attached to the handpiece; and detection by determining time of travel of signals from a transponder in the handpiece to a fixed reference plane.

38 Claims, 24 Drawing Sheets

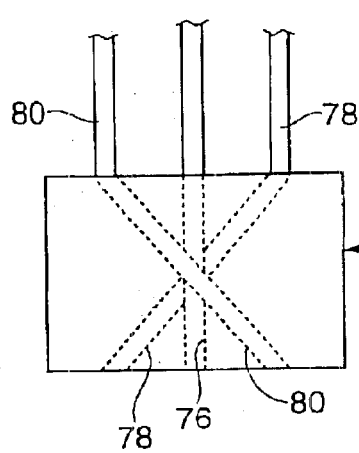
FIG. 15A
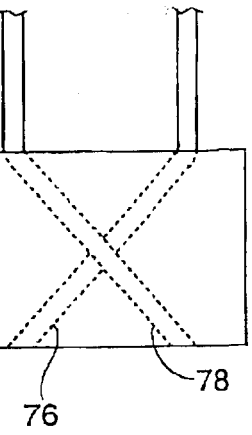
FIG. 15C
FIG. 15B
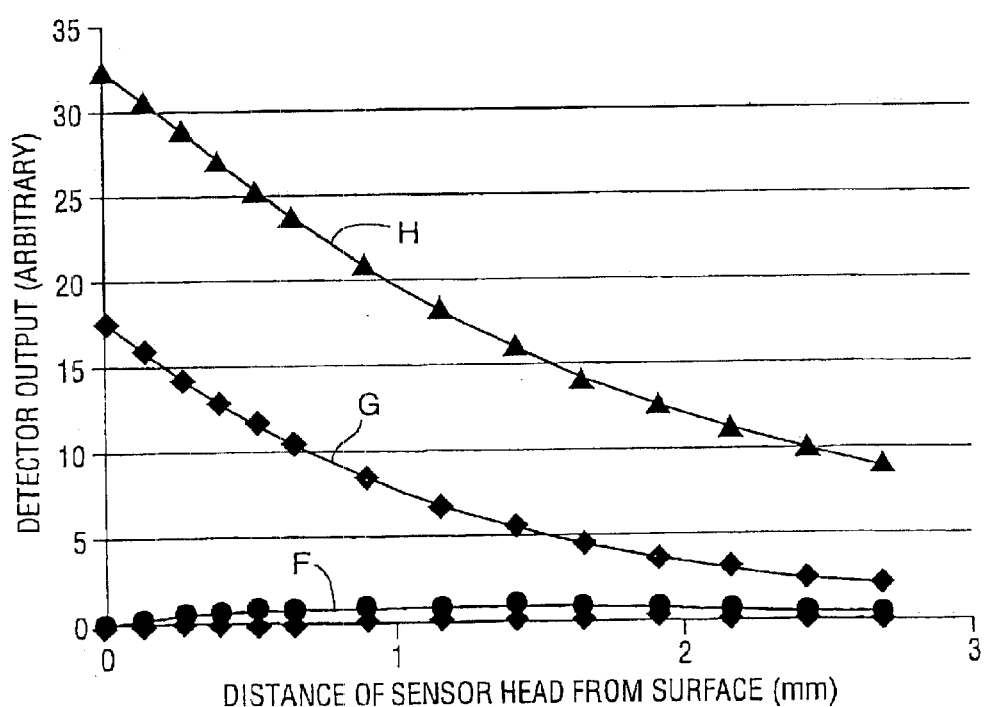
FIG. 15D

AUTOMATIC FIRING APPARATUS AND METHODS FOR LASER SKIN TREATMENT OVER LARGE AREAS

TECHNICAL FIELD OF THE INVENTION

The present invention relates in general to apparatus for laser skin treatment, such as depilation. The invention relates in particular to an automatic repeat firing system for laser skin treatment apparatus which, in a single firing, can treat only a relatively small sub-area of an area of skin to be treated.

DISCUSSION OF BACKGROUND ART

In laser dermatological treatment operations such as depilation, an area of skin to be treated may often be much greater than the area which can be treated by a single firing of laser apparatus. Typical apparatus for laser treatment includes a handpiece for delivering laser radiation from a laser to skin being treated. The laser may be remote from the handpiece with the laser radiation being delivered to the handpiece via an optical fiber or articulated arm. Alternatively, the laser radiation may be provided by a diode-laser array incorporated in the handpiece. A handpiece is often furnished with a cooled window which is placed in contact with the skin, laser radiation being delivered to the skin through the cooled window.

Treatment of a large area of skin is typically accomplished by an operator manually firing the laser apparatus, with the handpiece located in one position on the area of skin being treated, then moving the handpiece to another position in the treatment area and manually firing the laser apparatus again. One disadvantage of this method is that it can be difficult to precisely and contiguously locate treated sub-areas of the total area being treated such that no sub-area is left untreated and no overlapping of treated sub-areas occurs. Another disadvantage of this method is that time taken to relocate the handpiece from a treated sub-area to an adjacent untreated sub-area can prolong the treatment operation. This, in turn, can lead to an increased cost of the operation. The apparatus and method of the present invention is intended to overcome these disadvantages.

SUMMARY OF THE INVENTION

The present invention is directed to a method of treating an area of skin with a laser by delivering a series of laser-radiation pulses to the skin. Each of the laser pulses treats a sub-area of the area to be treated.

In one aspect of the present invention, a laser is provided which, on being fired, generates a pulse of laser-radiation. A handpiece is provided and arranged for delivering a pulse of laser-radiation from the laser to the skin being treated.

While the handpiece is being moved over the skin being treated, the location of the handpiece in the area of skin being treated is electronically determined, and the laser is automatically fired when the electronically determined location corresponds to a sub-area to be treated.

The terminology "automatically fired" here means that as the firing of the laser is electronically triggered by the electronic position determination without operator intervention other than moving of the handpiece. The terminology "laser" means a laser resonator including a gain medium (which may be a diode-laser or array of same) and those electrical and electronic circuits needed to power the laser and to switch or modulate the laser to provide the laser-radiation pulses.

In one embodiment of the present invention the location determining step includes providing a plurality of regularly spaced indicia on or adjacent the area of skin being treated. At least one sensor is provided on the handpiece and arranged to detect passage of the handpiece by one or more of the indicia as the handpiece is moved over the skin being treated. The automatic firing is triggered by the passage of the handpiece by one or more of the indicia. The indicia may be graphic indicia, magnetic indicia, or mechanical indicia.

In one example of this preferred embodiment of the present invention, the indicia are graphic (optically detectable) indicia. The sensor includes a light-source arranged to direct light onto the skin being treated such that the thus directed light is scattered by the skin being treated. The sensor includes one or more light detectors arranged to detect the light scattered by the skin. The graphic indicia are equally-spaced parallel lines drawn on the area of skin being treated in a medium which is opaque to the wavelength of light emitted by the light-source and transparent to the wavelength of said pulse of laser radiation. Passage of the handpiece by any one of the indicia (crossing any one of the lines) results in a reduction in the scattered light detected by the detector. The reduction in scattered light indicating that one of said indicia has been passed, i.e., a line has been crossed.

In another embodiment of the present invention the location determining step comprises providing a roller on the handpiece, the roller being-arranged to contact the skin being treated and rotate in response to the handpiece being moved over the skin being treated. The roller has a plurality of regularly spaced indicia thereon. At least one sensor is provided on the handpiece. The sensor is arranged to detect passage by the sensor of one or more of the indicia as the roller rotates. The automatic firing is triggered by the passage by the sensor of one or more of the indicia.

The indicia on the roller may be radially extending lines on a side of the roller or longitudinally extending lines on a cylindrical surface of the roller. The indicia in either case may be graphic (optically detectable) indicia or magnetic (magnetically detectable) indicia. In one variation of this embodiment, indicia can be omitted from the roller and the roller axially connected to a shaft encoder, the shaft encoder providing signals used for the electronic position determination.

In yet another embodiment of the present invention, the location determining step comprises providing a screen adjacent the skin being treated. A transponder is provided on the handpiece. The transponder is arranged to emit a regular train of signal-pulses toward the screen such that the signal-pulses are incident thereon and a return-pulse corresponding to each of the incident signal-pulses returns to the handpiece. A receiver is provided on the handpiece for receiving the return pulses. An elapsed time between emitting a signal-pulse and receiving a corresponding return-pulse is determined. The elapsed time is representative of the location of the handpiece.

The signal-pulses are preferably ultrasonic pulses. However, the use of other forms of signal pulses is possible, for example optical pulses or radar pulses.

In still another embodiment of the present invention the location determining step also includes providing a transponder on the handpiece. The transponder is arranged to emit a regular train of signal-pulses each thereof in diverging beam. At least two spaced-apart receivers are provided. The receivers are located in a position remote from the handpiece, within the divergence of the beam, for receiving said signal pulses. Based on the spacing of the receivers and an arrival time of the signal pulses at the receivers, the location of the handpiece is determined in at least length and width dimensions of the area of skin to be treated. For an area of skin to be treated which is contoured, three spaced-apart receivers may be provided, and the location of said handpiece in the area of skin to be treated determined in length width and height dimensions.

In another aspect of the present invention, the handpiece may be equipped with a skin contact-sensor for determining whether or not the handpiece is in contact with skin being treated. This is useful in laser skin treatments wherein laser radiation is delivered to the skin via a lens or transparent body (applicator) incorporated in the handpiece and in contact with the skin for promoting efficient coupling of laser radiation into dermal layers.

In one preferred embodiment of skin-contact sensing in accordance with the present invention, a light-source is provided having an exit-aperture thereof on the handpiece. The exit-aperture is configured to be in contact with the skin being treated when the applicator is in contact with the skin being treated. Light from said light-source is delivered via said exit-aperture thereof such that, when the applicator is in contact with the skin, light delivered via the said exit-aperture is transported laterally through the skin via volume scattering of the light. A detector is provided having a receiving-aperture on the handpiece proximate the light-source exit-aperture. The output of the detector is monitored. The monitored detector-output is interpreted as an indication that the applicator of the handpiece has made or lost contact with the skin being treated.

The above-described skin contacting method is not limited to a handpiece delivering laser-radiation for skin treatment but is applicable to handpiece delivering electromagnetic radiation (for skin treatment) from an incoherent source such as a flashlamp. An above-described sensor for detecting graphic indicia may be configured to additionally function as a skin sensor for implementing the above-described skin-contact sensing method.

Preferred embodiments of the present invention are described in detail hereinbelow with reference to a laser hair removal apparatus using an array of diode-lasers. Automatic firing arrangements in accordance with the present invention are neither limited to apparatus including diode-lasers, nor limited to hair removal apparatus. Those skilled in the art will recognize that automatic firing principles of the present invention are applicable to laser apparatus including other laser types, for example, solid-state lasers, to apparatus wherein treatment light is provided by an incoherent source of electromagnetic radiation such as a flashlamp, and to other laser skin treatments, for example, treatment of vascular lesions such as "port wine" stains.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

FIGS. 15A and 15B are, respectively, side and front elevation views schematically illustrating details of a skin-contact sensor head for the handpiece of FIGS. 14 and 15.

FIG. 15C is a front elevation view schematically illustrating details of an alternative skin-contact sensor head for the handpiece of FIGS. 14 and 15.

FIG. 15D is a graph schematically illustrating detector output as a function of distance from various surfaces of a skin-contact sensor head in accordance with the arrangement of FIG. 15C.

DETAILED DESCRIPTION OF THE INVENTION

Figure 1:
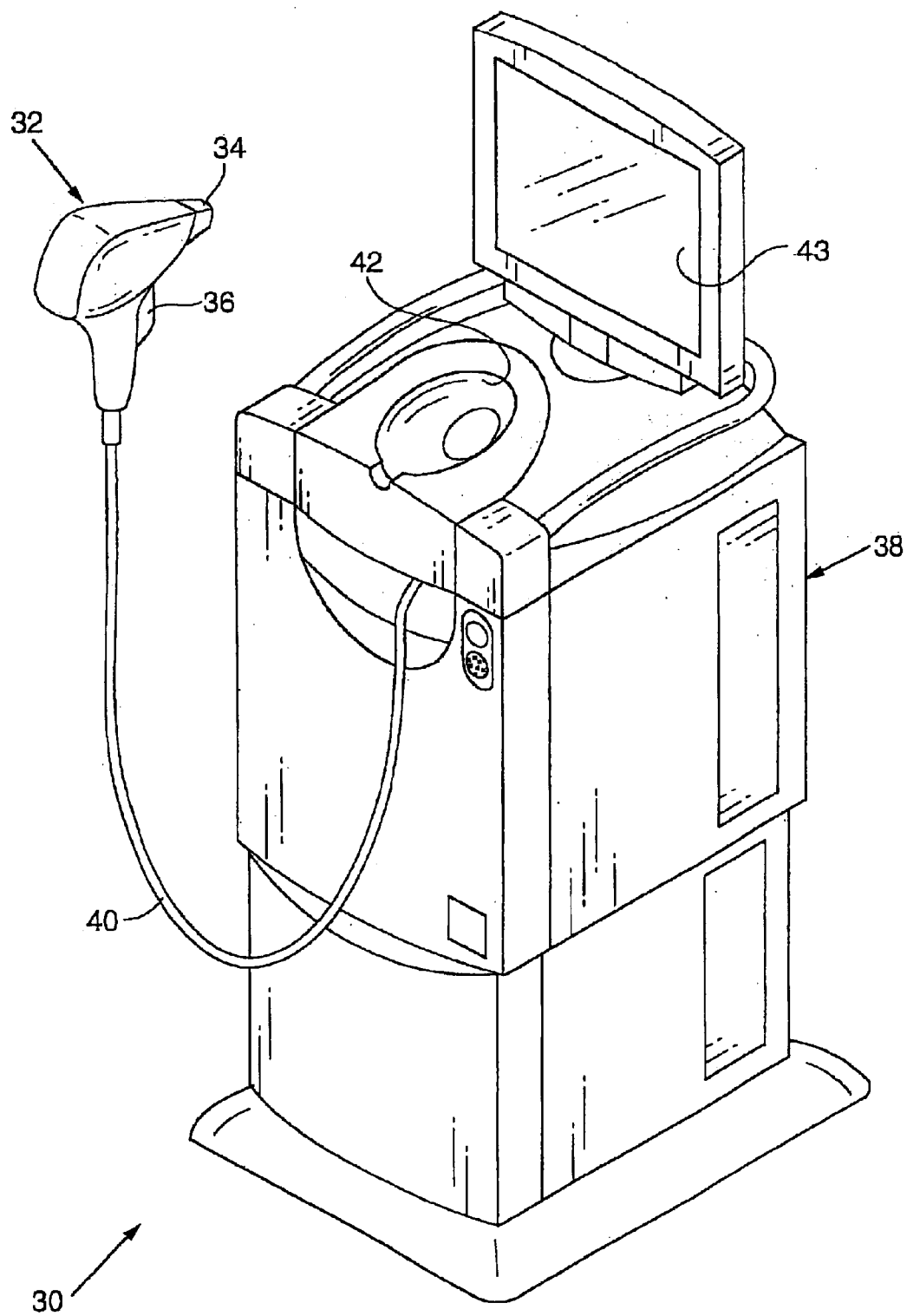
FIG. 1 is a perspective view schematically illustrating a first preferred embodiment of laser treatment apparatus in accordance with the present invention having a first handpiece including a chilled tip and having a position sensor located therein, the handpiece being movably connected to a control console for controlling operating parameters of the apparatus.

Turning now to the drawings, wherein like features are designated by like reference numerals, FIG. 1 depicts a first preferred embodiment of laser skin treatment apparatus 30 in accordance with the present invention. Apparatus 30 includes a handpiece 32 including a diode-laser array (not shown in FIG. 1) for providing laser radiation for treatment. The diode-laser array is alternatively referred to hereinafter simply as the laser. The diode-laser array emits at a wavelength between about 790 and 830 nanometers (nm). This wavelength range should not be construed, however, as limiting the present invention.

In a tip 34 of handpiece 30 are located optical apertures of a position sensor incorporated in the handpiece. The apertures and other components of the position sensor are not shown in FIG. 1 but are described in detail further hereinbelow. The handpiece is activated by a trigger 36.

Apparatus 30 includes a control console 38. Control console 38 includes, inter alia, power-supplies, a water-supply and control electronics for components of handpiece 32. The control electronics and power and water supplies are connected to handpiece 32 via an umbilical sheath 40. When not in use, handpiece 32 may be "parked" in a receptacle 42 in control console 38. The operating sequence and treatment parameters for the apparatus are controlled from a touch-screen display 43.

Figure 2:
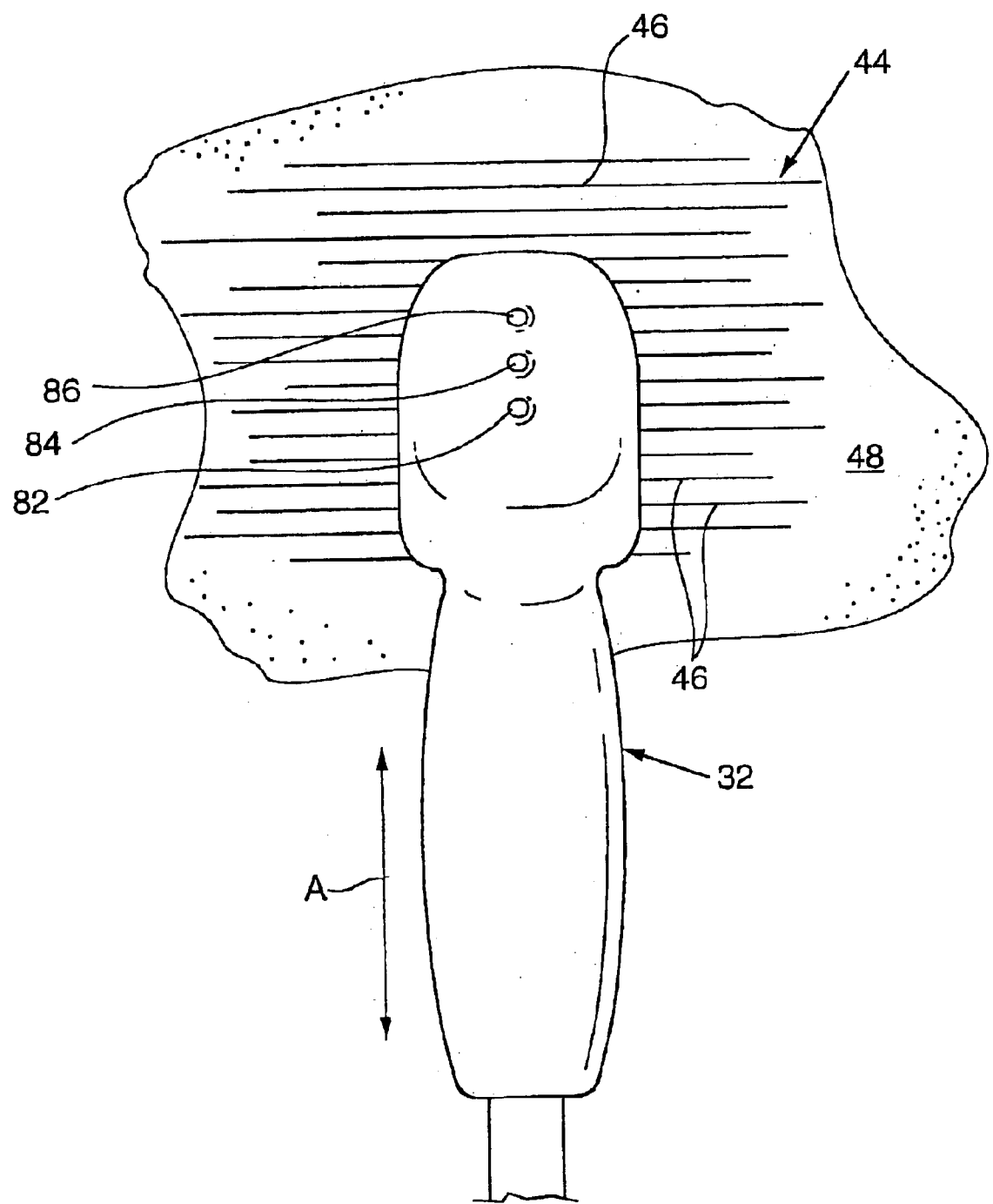
FIG. 2 is a rear elevation view of the handpiece of FIG. 1 schematically illustrating the handpiece being moved in a direction orthogonal to a regular grid of parallel lines drawn on an area of skin being treated.

Referring now to FIG. 2, in one preferred method of operating apparatus 30, a grid 44 of equally-spaced parallel lines 46 is drawn on skin 48 being treated. The grid preferably covers the entire area of skin on which treatment is desired. Lines 46 are preferably spaced apart by a distance equal to a linear dimension of the area treatable in a single is firing of the laser or a sub-multiple of that dimension. Preferably, the area treatable in a single laser firing is made square, or at least rectangular, in which case the spacing of lines 46 is made equal to the width or length of the area or some sub-multiple thereof. Handpiece 32 is moved in a direction orthogonal to lines 46 as indicated by arrows A, with tip 34 of the handpiece in contact with skin 48.

When the handpiece is initially applied to the skin, the output of detectors 72 and 74 (FIG. 3) is stored by the control electronics of console 38 to form a baseline reading. This baseline reading will vary depending on the skin reflectivity at the illuminating wavelength and will be lower for darker skin types. The detection of lines on the skin is based on a drop in detector output below a predetermined fixed percentage of this baseline reading. As handpiece 30 is moved over skin 48 the position sensor of the detectors and control electronics detect the crossing of a line 46 and firing of the laser is triggered.

When apparatus 30 is in the automatic firing mode, depressing trigger 36 on handpiece 32 acts to enable automatic firing of the laser. The laser will not fire, regardless of detected line crossings, unless trigger 36 is also depressed.

After reaching an extreme one of lines 46, handpiece 32 is moved laterally by the width of the area treatable in the single laser firing, and handpiece 32 is again moved in the direction indicated by arrows A. The foregoing sequence is repeated until the desired area is treated. Movements of handpiece 32 in the direction indicated by arrows A may be all made in the same direction, or alternating between forward and reverse directions.

Figure 3:
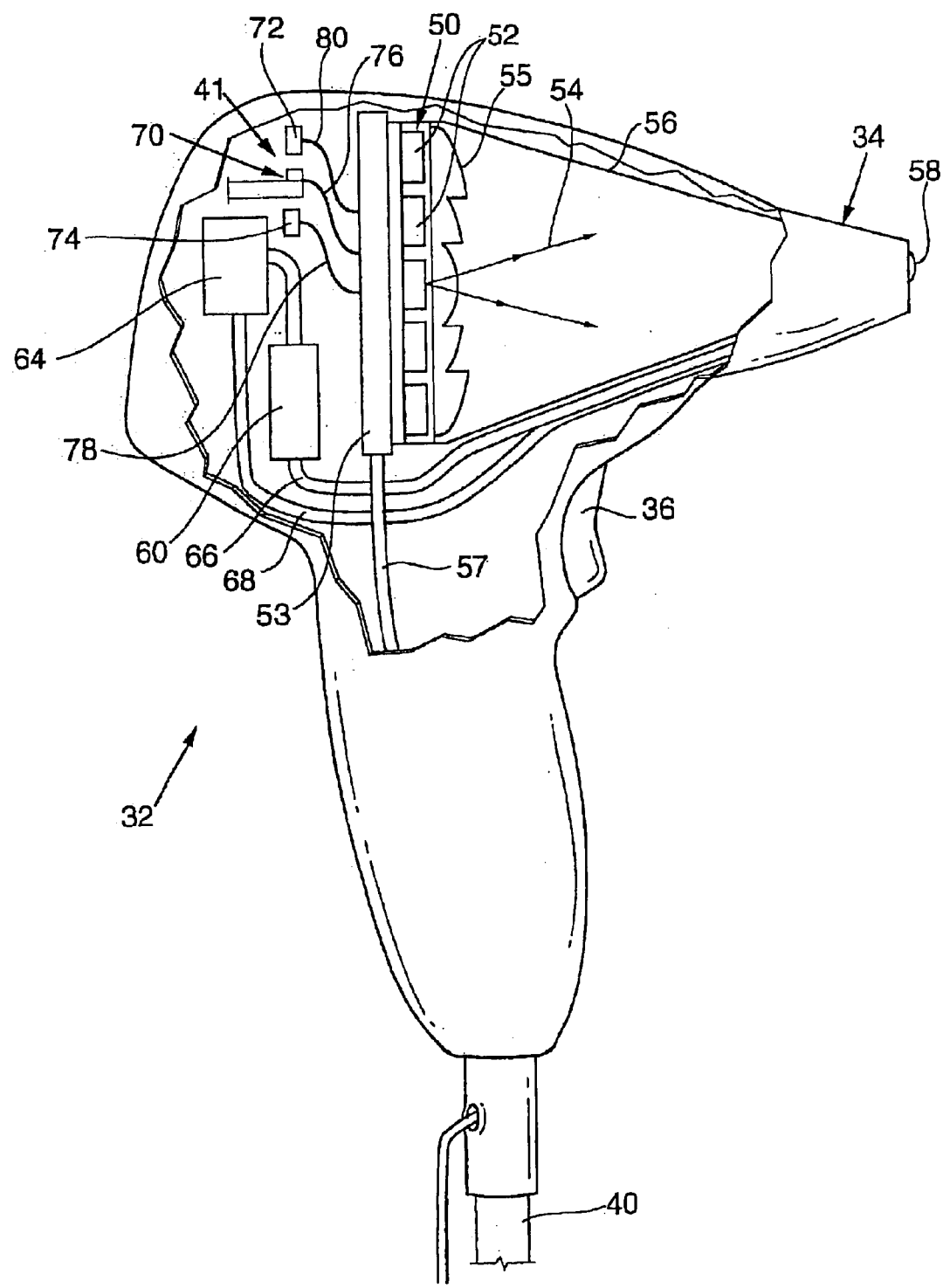
FIG. 3 is a partially-cutaway side elevation view of the handpiece of FIG. 1 schematically illustrating a light-source and photodetectors of the position sensor for respectively sending light to and receiving light from optical apertures in the tip of the handpiece.
Figure 4:
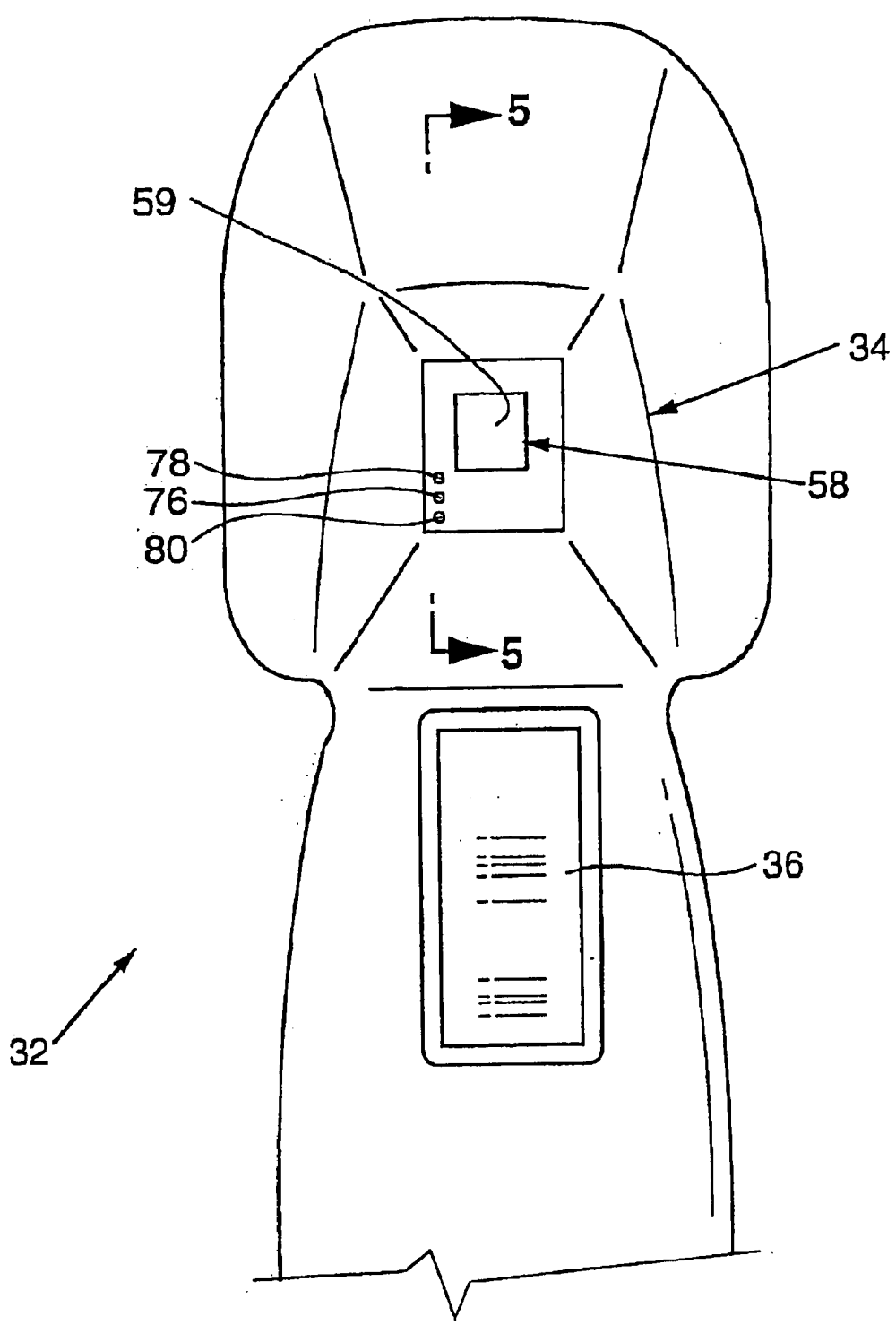
FIG. 4 is a partial front elevation view of the handpiece of FIG. 1 schematically illustrating details of the chilled tip of the handpiece and optical apertures of the sensor therein.
Figure 5:
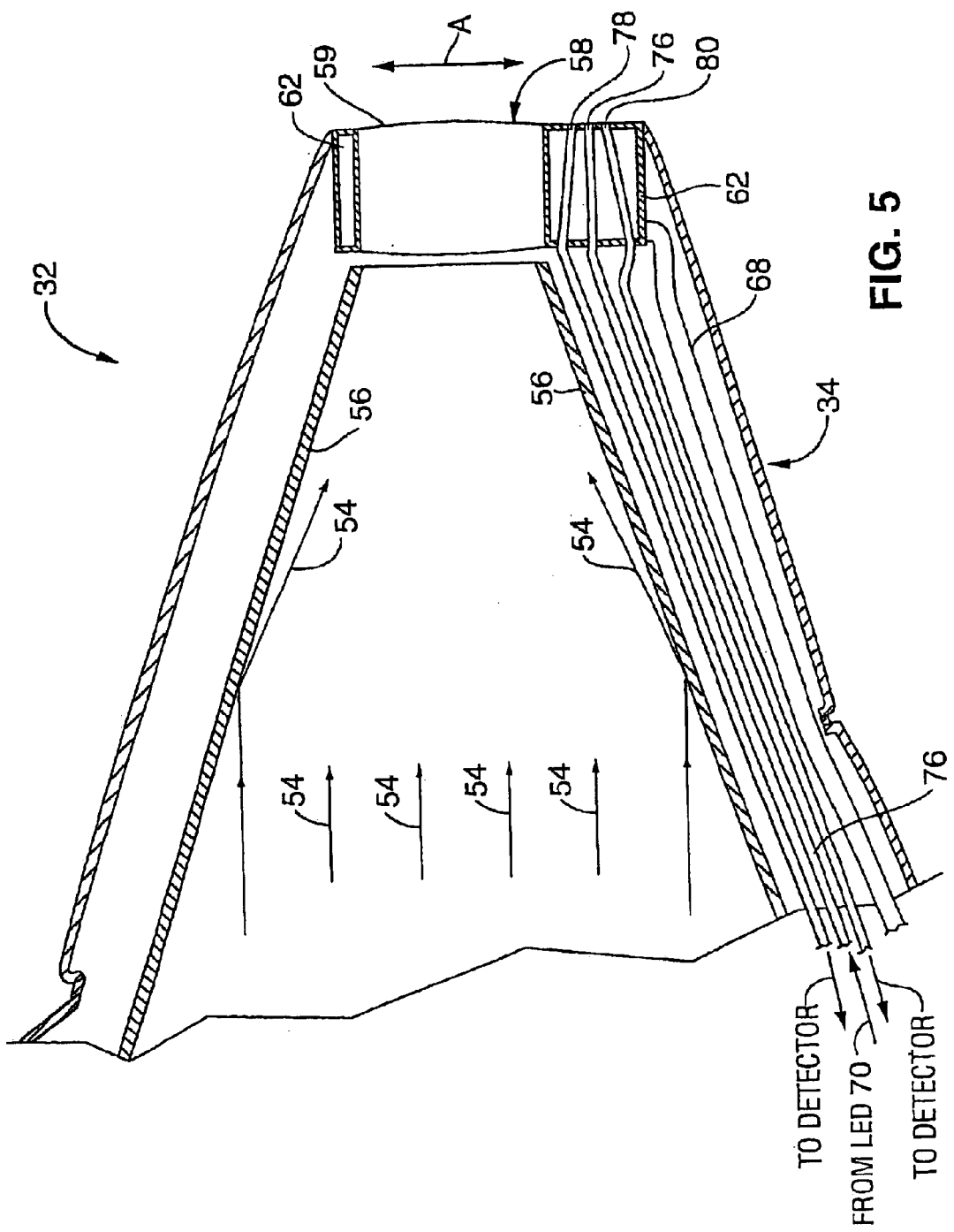
FIG. 5 is a partial cross-section view of the handpiece of FIG. 1 seen generally in the direction 5—5 of FIG. 4 and schematically illustrating further details of the position sensor in the handpiece.

Referring next to FIG. 3, FIG. 4 and FIG. 5, further details of handpiece 32 and, in particular, of the position sensor therein (designated by numeral 41 in FIG. 3), are described. As noted above, handpiece 32 includes a diode-laser array. In a preferred example, a diode-laser array 50 includes a total-of ten diode-laser-bar stacks 52 arranged into rows of five. Each diode-laser-bar stack has a total of nineteen individual edge-emitting diode-lasers. The diode-lasers emit light at a wavelength between about 790 and 830 nanometers (nm). Diode-laser array 50 is assembled on a water-cooled backing-plate 53. Water is supplied to backing-plate 53 from control console 38, via a conduit 55 extending through umbilical sheath 40. Arranged in this way, diode-laser array 50 can deliver up to 1600 Watts (W) of laser-radiation.

Laser-radiation 54 from diode-laser array 50 is converged in the fast axis of the diode-laser bars by cylindrical microlenses (not shown) associated with diode-laser-bar stacks 52, and converged in the slow axis of the diode-laser bars by a Fresnel lens 55. The laser radiation is then guided by a tapered light-guide 56 toward a lens 58, preferably of sapphire, in tip 34 of handpiece 32. Lens 58 most preferably has a square aperture to facilitate "tiling" together of sub-areas treated by single firings of the laser as described above with reference to FIG. 2.

Lens 58 has a contact surface 59 and is cooled by a cooling-fluid, preferably a mixture of water and ethylene glycol, chilled by a thermo-electric cooler (TEC) 60 (see FIG. 3). The cooling-fluid is circulated through a copper microchannel-cooling jacket 62 (see FIG. 5) in thermal contact with lens 58. Circulation of the cooling-fluid is effected by a pump 64 via delivery and return conduits 66 and 68 respectively (see FIG. 3).

Sensor 41 includes a light-source 70 (see FIG. 3), preferably a semiconductor light-source, such as a light-emitting diode (LED) or the like, and two photodetectors 72 and 74, such as photodiodes. These photodetectors are connected via electrical connections (not shown) through umbilical sheath 40 to control electronics in console 38.

Light from light-source 70 is guided by an optical fiber 76 to tip 34 of handpiece 32 (see FIGS. 3, 4 and 5). Light exiting optical fiber 76 incident on skin 48 is scattered through upper layers of the skin. A portion of the scattered light enters optical fibers 78 and 80 on opposite sides of optical fiber 76. The end faces of optical fibers 76, 78, and 80 can be considered as apertures of the position sensor 41 of handpiece 32. Preferably these end faces are equally spaced in a straight line as shown in FIG. 4. Optical fibers 76, 78, and 80 can be considered as having proximal ends thereof adjacent light-source 70 and detectors 72 and 74 respectively, and distal ends thereof in tip 34.

It is also most preferable that the optical-fibers are arranged at an angle to each other in tip 34 of handpiece 32. The angle converges towards the distal ends of the fibers. The angle is selected to minimize the possibility of light from optical fiber 76 entering optical fibers 78 or 80 by specular reflection from any surface. One arrangement found to be optically effective and mechanically convenient is that the fibers 78, 76 and 80 have a diameter between about 0.5 and 1.5 millimeters (mm) and are set at the following angles: 0 degrees, 15 degrees, and 30 degrees from the vertical (perpendicular to skin 48). The distal ends of the fibers are preferably as close to each other as is consistent with securely retaining them in the sensor head. One reason for this is discussed further hereinbelow.

It is important that lines 46 are drawn with a medium (ink, paint or the like) which is transparent to laser-radiation 54 from diode-laser array 50, but absorbent for light from light-source 70. Light from light-source 70 must also be able to penetrate skin 48. By way of example, it has been found that for laser-radiation having a wavelength between about 790 and 830 nm, and a light-source 70 in a form of a LED emitting at a wavelength of about 660 nm, an ink containing the dye "Basic Blue 1" (CAS number 3251-06-0) is effective as a medium for lines 46.

Continuing now with particular reference to FIGS. 2 and 5, when end faces of optical fibers 76, 78 and 80 in tip 34 of handpiece 32 are all in contact with skin 48 in a region thereof between lines 46 (or outside grid 44 altogether) both optical fibers 78 and 80 will receive scattered light from optical fiber 76. The light so received will be transmitted to detectors 72 and 74. Control electronics connected to the detectors will record what may be described as a bright condition of the detectors.

As handpiece 32 is moved in the direction indicated by arrows A, either optical fiber 78 or optical fiber 80 will pass over a line 46 depending on the direction of movement (forward or reverse) of handpiece 32. If the width of lines 46 is equal to or greater than the diameter of the optical fibers, the optical fiber instantly over the line 46, and the detector associated therewith, will receive less scattered light because of the absorption of the line-marking medium. In this case, the control electronics will record a dark condition for that detector. Providing two detectors and associated optical fibers, arranged as shown and discussed provides the control electronics with a means of determining the direction of travel of handpiece as discussed below.

The control electronics are preferably programmed to record a "line-crossing" only after both detectors 74 and 72 have registered a dark condition, in sequence. The sequence in which the dark conditions occur determines the direction of travel. The recorded line-crossing is used by the control electronics to trigger a firing of the laser for treatment. The number of line-crossings recorded can be used to establish a position of tip 34 of handpiece with respect to a starting (datum) point or line.

Another advantage of providing the above-discussed two detectors and fibers is in providing a means for determining whether or not tip 34 of handpiece 32 is in contact with skin 48. If tip 34 loses contact with skin 48, detectors 72 and 74 will simultaneously register a dark condition. Control electronics can be programmed to use such a recorded simultaneous dark condition to prevent firing of the laser either automatically or manually, thereby preventing, for example, firing the laser in an attitude where it may be therapeutically ineffective.

The time interval between line-crossings can be used to determine the speed of travel of tip 34 of handpiece 32 over skin 48. One reason for requiring knowledge of the speed of travel is to prevent handpiece 32 from being moved so quickly that, at the maximum practical firing rate of diode-laser array 50, sequentially treated sub-areas of skin 48 can not be contiguous. By way of example, in above-described apparatus 30, the maximum firing rate is between about four and eight Hertz (Hz). Another reason is that too rapid a motion can reduce the effectiveness of chilled lens 58 in cooling skin to be treated.

To optimally prevent such occurrences, it is desirable to know the speed of travel of the handpiece before it has moved completely out of a last-treated sub-area of skin 48, and preferably also before the laser is first fired. This can be achieved by spacing lines 46 at some sub-multiple of the width (or length) of a treated sub-area, for example at one-half or one-third that width. Correspondingly, respectively two or three sequential line-crossings will need to be recorded by the control electronics of console 38 in order to trigger a laser firing, while consecutive recorded sequential line-crossings are used to determine the speed of travel of handpiece 32.

From the speed of travel determination, it is possible to provide a simple audible or visual warning of excess speed of travel and even to prevent firing of the laser if a predetermined speed threshold is exceeded. Referring again to FIG. 2, a simple visual display may take the form of three different colored LEDs 82, 84, and 86, located on the back of handpiece 32, these diodes being activated, for example, according to whether the rate of travel is respectively slower than optimal, optimal, or faster than optimal. Those skilled in the art may devise other speed display forms without departing from the spirit and scope of the present invention such as an (apparently) moving bar type or "thermometer" type display of the type often used for sound level indication in electronic sound recording apparatus.

Reasons for preventing a laser firing, be they related to speed of travel or lack of contact, and the position at which firing was prevented can be displayed on display 43 of console 38. This provides that an operator can correct the reasons for prevention of firing and resume automatic firing at the point of termination, or treat individual untreated sub-areas, one by one, by manually firing the laser.

It is pointed out here that instead of lines drawn in a medium which is darker than the skin as discussed above, it is also possible to employ an medium (ink) containing a fluorescent agent such as fluorescein (resorcinolphthalein, $C_{20}H_{12}O_5$). When excited by light, for instance from a light-source (LED) 70, having a wavelength centered near 494 nm, fluorescein emits light centered at 520 nm. A detector with a matched filter, for example an interference filter having a passband full width at half maximum transmission (FWHM) of 10 nm, at a peak transmission wavelength of 520 nm, can selectively detect this fluorescent emission. Here, since light emission is being detected rather than light absorption, line crossings can be detected equally effectively on skin of any natural color.

It should be noted, here, that in this specification, it is contemplated, unless otherwise stated, that any computation or signal evaluation required for position determination, laser firing decisions and the like is accomplished by one or more electronic processors in control circuitry of console 38. Communication for this purpose with devices incorporated in handpiece 32 and any below described variations thereof is accomplished via umbilical sheath 40 as exemplified above. Any remote displays or sensor devices are assumed to be connected directly to control electronics of console 38. It is emphasized, here, that this assumption is made at least for convenience of description and should not be considered limiting. Those skilled in the art will recognize that processing devices could be located remote from console 38, proximate devices in which electronic control is required, for example, in a handpiece 32, or in a computer such as a personal computer (PC). Should such remote processing devices be used, the manner of interconnection of the processing devices will be evident to those skilled in the art from the functional descriptions of embodiments presented herein.

Continuing now with a description of other preferred embodiments of the present invention, a preferred apparatus and method of the present invention is described above in terms of automatic firing by detecting crossings of lines in a parallel grid of lines drawn on skin to be treated with manual lateral shifting of handpiece 32 between linear automatic firing sequences. In another preferred method and apparatus in accordance with the present invention, automatic firing is provided for both longitudinal and lateral movement of handpiece 32. A brief description of this method and apparatus is set forth below with reference to FIG. 6 and FIG. 7

Figure 6:
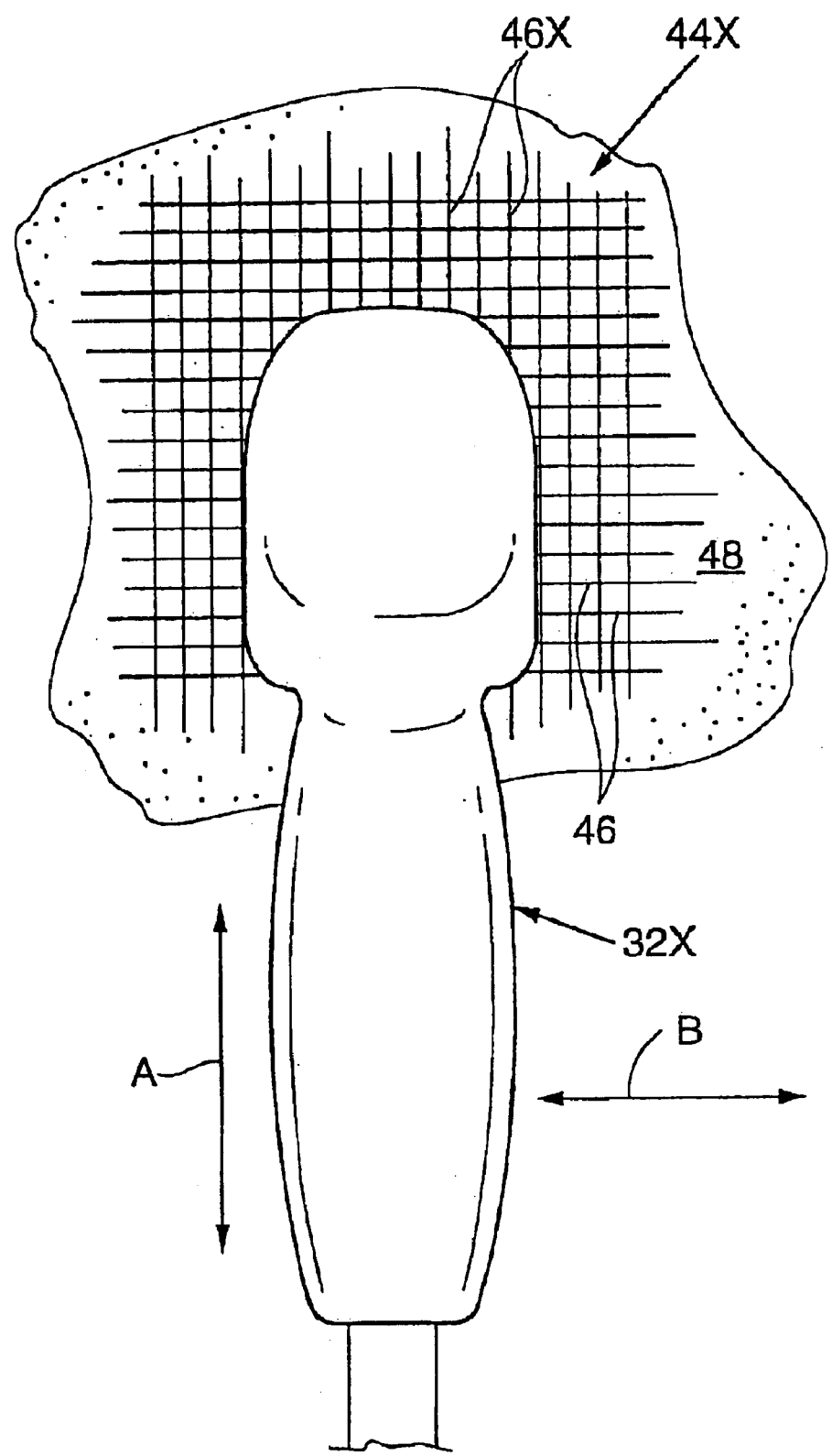
FIG. 6 is a rear elevation view schematically illustrating a second handpiece in accordance with the present invention arranged for automatic firing in both longitudinal and lateral directions of motion thereof.

Referring first to FIG. 6, a grid 44X is drawn on skin 48 being treated using a medium of the types discussed above. Grid 44X comprises above-discussed equally-spaced parallel lines 46 and, additionally, another set of equally-spaced parallel lines 46X orthogonal to lines 46. Lines 46 and 46X are preferably spaced apart by a distance equal to respectively the length and width of the area treatable in a single firing of the laser or a sub-multiple of that dimension. If the area treatable in a single laser firing is made square, of course, the spacing of lines 46 and 46X is equal. Longitudinal and lateral motion is designated in FIG. 6 by arrows A and B respectively.

Figure 7:
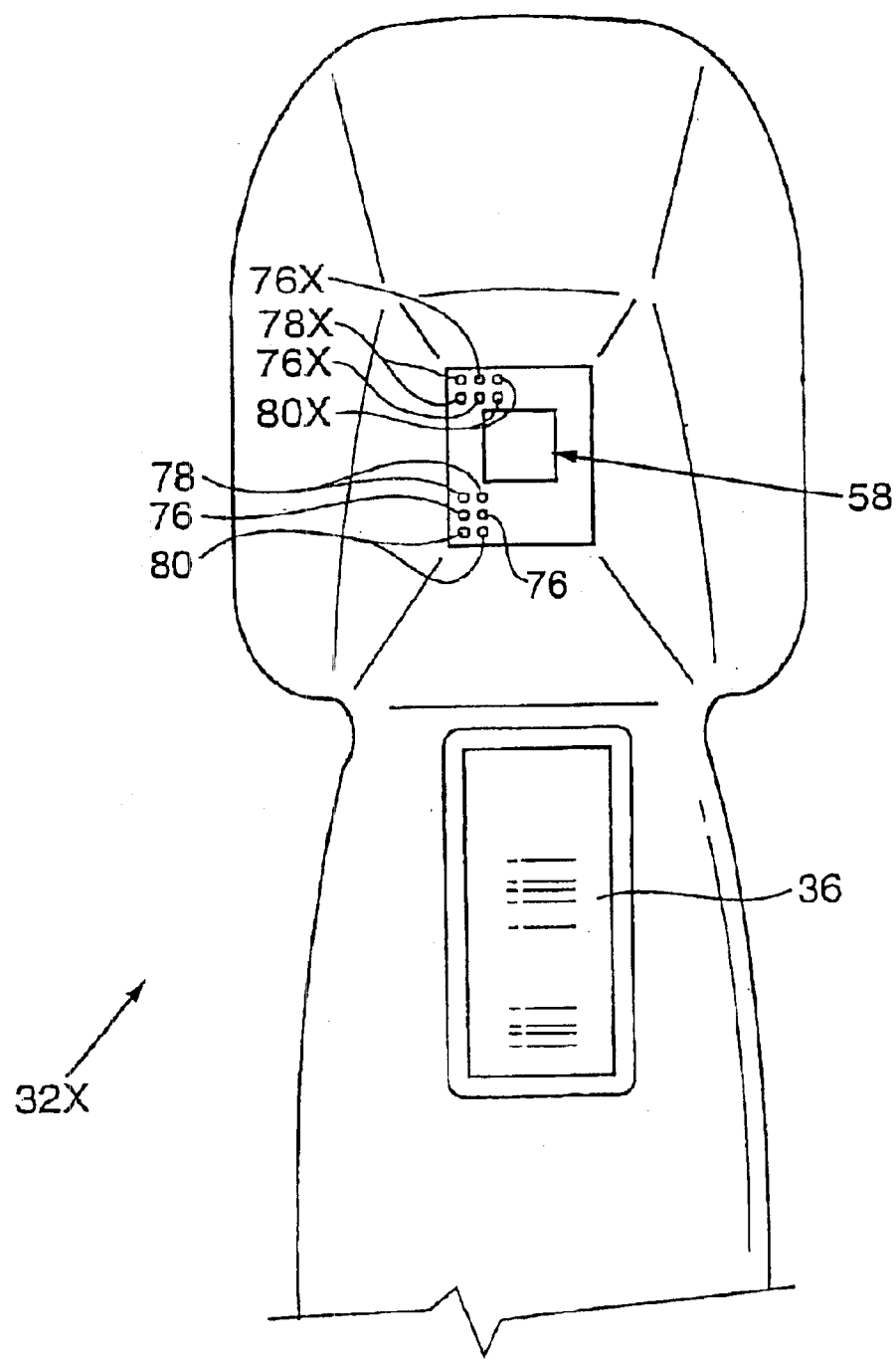
FIG. 7 is a partial front elevation view of the handpiece of FIG. 6 schematically illustrating details of the chilled tip of the handpiece and optical apertures of four position sensors therein.

Referring now to FIG. 7, a handpiece 32X for practicing the method of FIG. 6 includes at least one additional sensor (not shown), similar to above-described sensor 41 but arranged to detect lateral line-crossings. In such a lateral line-crossing sensor, apertures of the sensor would be aligned orthogonal to those of above described sensor 41. This is illustrated in FIG. 7 by apertures (optical fiber ends) 78X, 76X, 80X. Preferably, there are two (a pair of) sensors for each direction as illustrated in FIG. 7 by the additional sensor apertures. Apertures for each pair of sensors are parallel to each other and spaced apart, preferably by at least a width of a line 46 or 46X. This arrangement avoids problems that would be created by having only one set of sensors for a particular direction of travel aligned over a line in the direction intended for the sensor of the opposite direction.

From the above discussion, those skilled in the art will be able to devise electronic processing logic for interpreting information from such a set of sensors without further explanation. One such processing method, for example may include, displaying each therapeutically-effective, automatic firing of the laser as a square on display 43 of console 38, the position of the square corresponding to its position in grid 44X of FIG. 6. This would provide an instant visual indication of the existence and position of any spots which had not been effectively treated.

Figure 8:
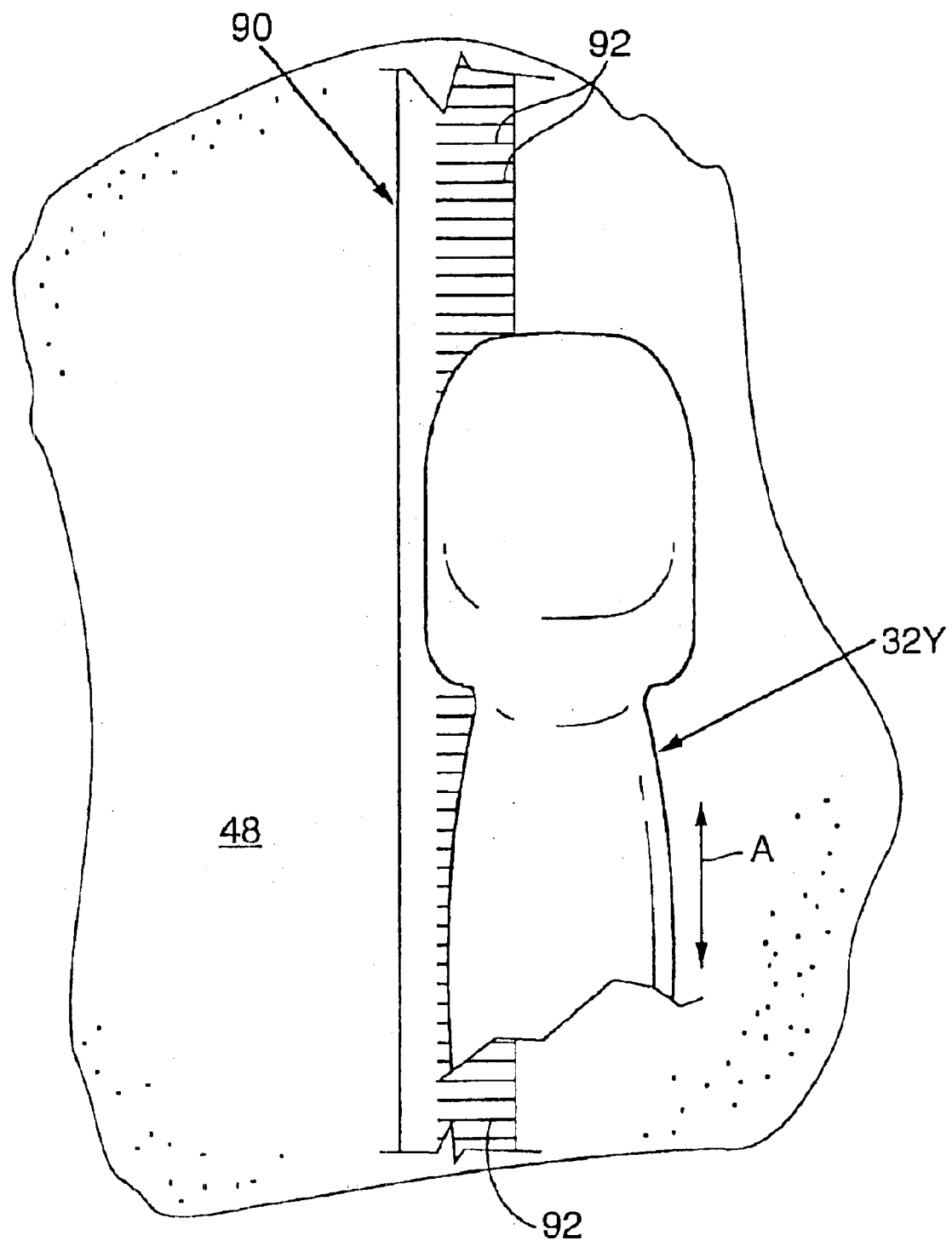
FIG. 8 is a partial rear elevation view schematically illustrating a third handpiece in accordance with the present invention arranged for automatic firing by sensing crossings of lines on a ruled guide-strip placed, rulings uppermost, in contact with skin being treated.

Referring now to FIGS. 8–11, in still another method of operating apparatus 30, a ruled strip 90 is placed, with equally-spaced rulings 92 thereof uppermost, on skin 48 to be treated (see FIG. 8). Rulings 92 are preferably spaced apart by a distance equal to a linear dimension of the area treatable in a single firing of the laser or a sub-multiple of that dimension, for reasons discussed above with reference to handpiece 32 of FIG. 2. Rulings 92 may also be arbitrarily spaced by some distance relatively small by comparison with the linear dimension of the area treatable in a single pulse, for example as small as the width of a ruling. This allows detection of many indicia crossings which can enable calculation of increasing or decreasing speed of movement of the handpiece.

A handpiece 32Y, with lens 58 thereof in contact with skin 38, is maintained in contact with strip 90 (see FIG. 11) and moved in a direction indicated by arrows A (see FIG. 8). Tip 34Y of handpiece 32 has its width reduced at its contact end to form steps 94 on each side thereof. Steps 94 preferably have a height just sufficient to allow horizontal surfaces 96 thereof to make contact with strip 90 when tip 34Y is in contact with skin 48 (see FIG. 11).

Handpiece 32Y includes at least one position sensor 41 (light-source and detectors thereof not shown in FIGS. 8–11) including an optical fiber 76 delivering light from the sensor's light-source and optical fibers 78 and 80 for transmitting light to the sensor's detectors. The optical fibers are threaded through handpiece 32Y and are held by a contact block 98 in the above-described alignment and angular relationship of sensor 41 of handpiece 32. Contact block 98 is attached to an extended portion 35 of handpiece 32Y. Extended portion 35 has a width equal to the width of tip 34Y across steps 94. Ends of optical fibers 76, 78 and 80 are held flush with base 102 of block 100 which is flush with horizontal surface 96 of step 94.

Strip 90 is preferably made from a translucent (bulk scattering) material, for example, a fluorocarbon polymer. Rulings 92 are made opaque to light from the light-source of sensor 41. It is also possible to use lines or rulings drawn on any diffuse reflector, for example, dark lines drawn on white (bright) paper or white, (bright) diffusely-reflective lines drawn on a black (dark) surface, i.e., a surface which absorbs light at the wavelength emitted by light-source 70. There is no requirement that the rulings be transparent to light from diode-laser array 50. Crossings of rulings 92 of strip 90 are detected and electronically processed in the manner described above with reference to the apparatus and method of FIG. 2. A crossing can be detected as a reduction in light detected by a detector 72 or 74, for example, in the case of dark lines on a bright background, or as an increase in the detected light, for example in the case of bright lines on a dark background.

Figure 9:
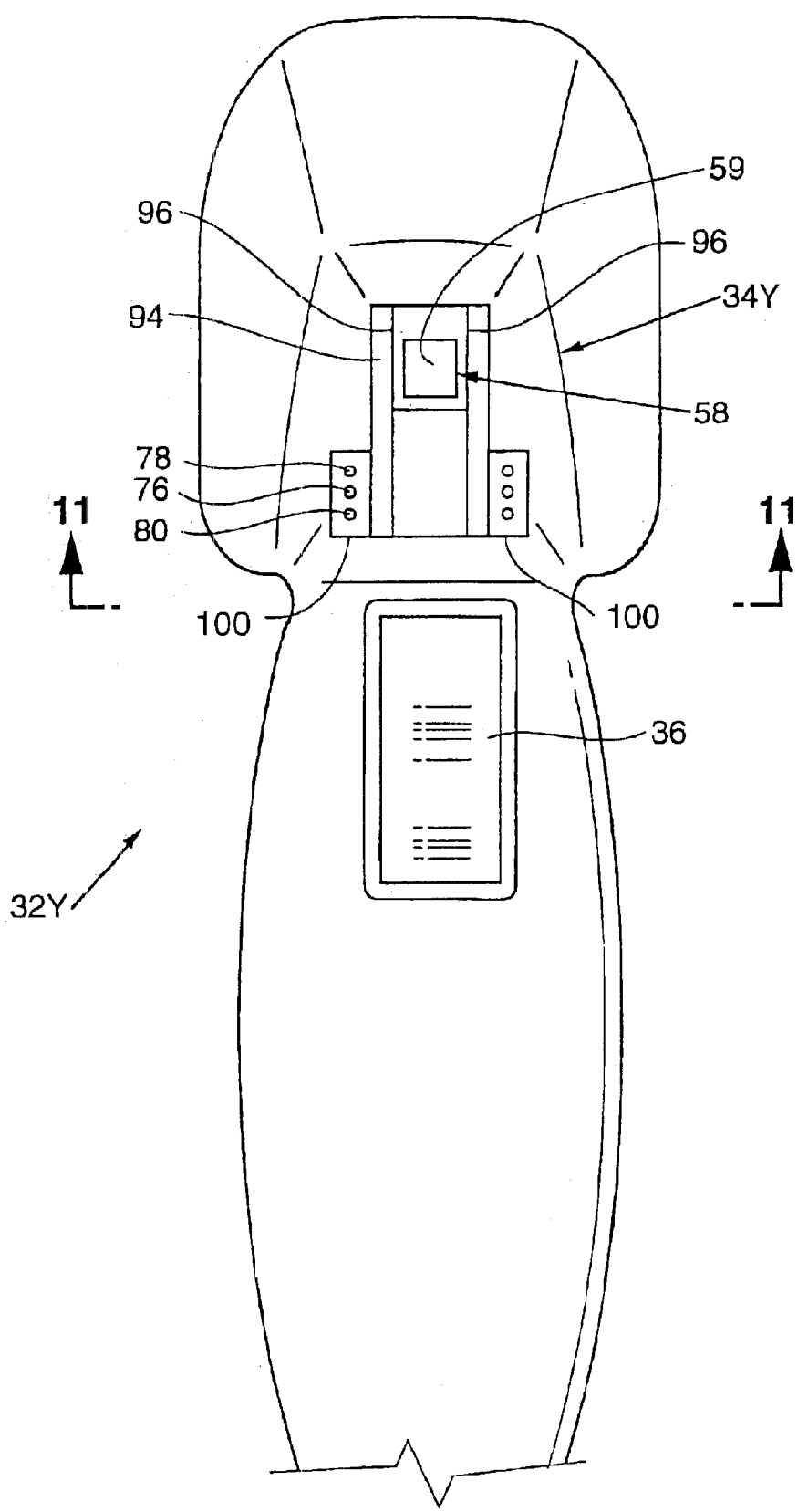
FIG. 9 is a front elevation view of the handpiece of FIG. 8 schematically illustrating details of position sensors for detecting the line-crossings.
Figure 10:
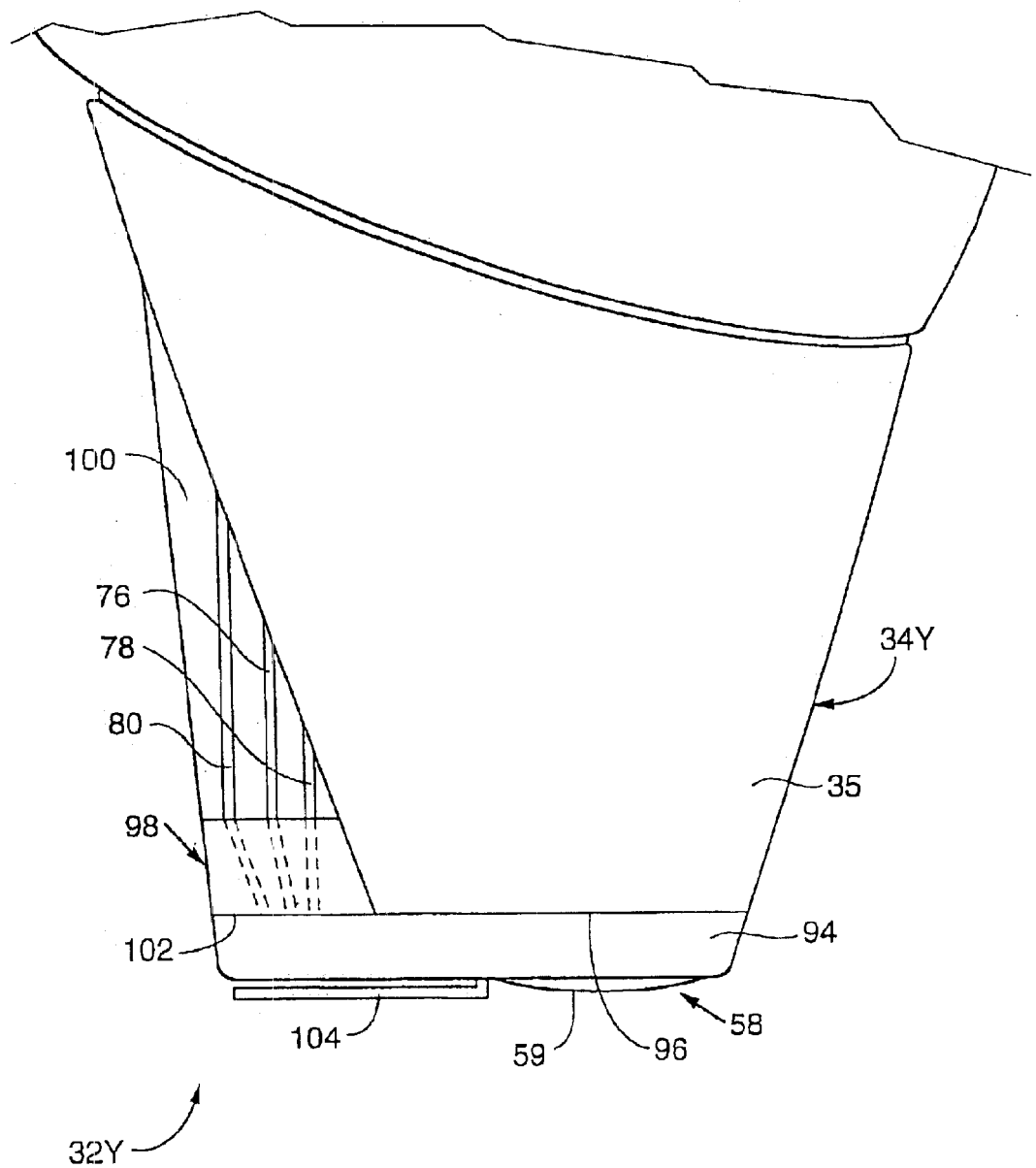
FIG. 10 is a partial side elevation view of the handpiece of FIG. 8, schematically illustrating further details of one of the position sensors for detecting the line-crossings.
Figure 11:
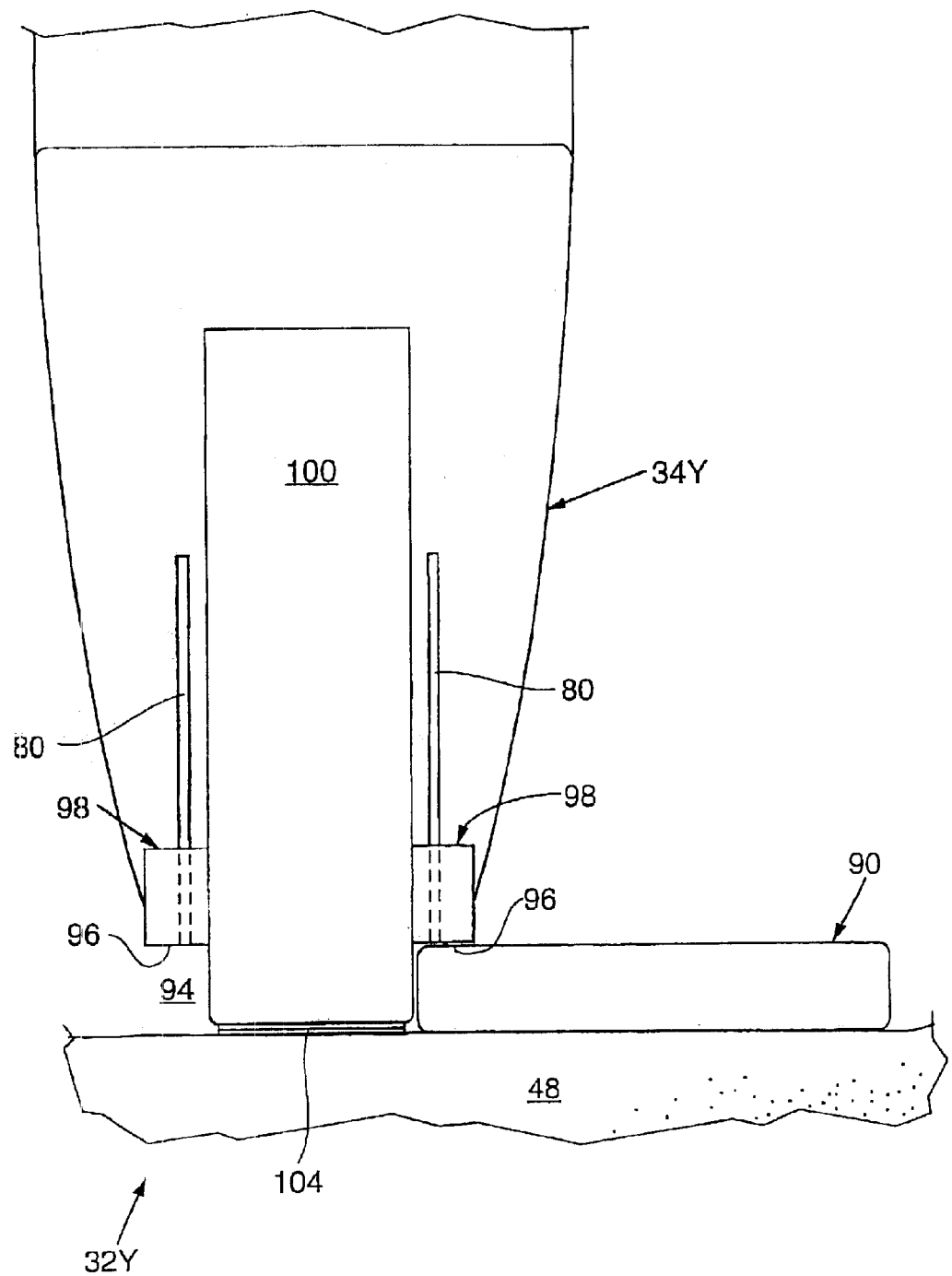
FIG. 11 is a partial plan view of the handpiece of FIG. 8 seen in the direction 11—11 of FIG. 9 and schematically illustrating further details of the position sensors for detecting the line-crossings and further details of the ruled guide-strip of FIG. 8.

Typically, the method of FIG. 8 is practiced by an operator holding strip 90 in position on skin 48 with one hand and moving handpiece 32Y with the other hand. As depicted in FIGS. 9–11, two position sensors 41 may be provided, with apertures of one sensor on one side of tip 34Y and apertures of the other sensor on the other side of tip 34Y. Selective activation of one or the other of the sensors provides for right or left hand operation of handpiece 32Y.

It should be noted here, that while position sensors 41 are described above with reference to a remote light-source and detectors optically communicating with sensor apertures by means of optical fibers, this should not be considered as a limiting configuration for such sensors. By way of example, in a handpiece similar to handpiece 32Y, a position sensor, logically functioning as described above, may be incorporated in a block of similar size and similarly position to block 100, with the light-source and detectors of the sensor incorporated in a single semiconductor chip.

The method of FIG. 8, using a separate guide strip rather than lines drawn on skin 48, permits that a position sensor may function by means other than optical. By way of example, a guide strip may be provided with magnetized rulings or indicia. This may be in the form of a preferentially magnetized strip of a form similar to that on credit cards and the like, or rulings in a magnetic medium on a strip of a non-magnetic material. One preferred sensor for such indicia would include at lest one and preferably two (for direction sensing) magnetic pickup heads located in a block of similar size and position to block 100. The two pickup heads would provide for a direction-sensing capability as described above for sensor 41. In another example, rulings or indicia 92 may be in the form of depressions in (or protrusions above) the upper surface of guide strip 90 with the indicia being sensed by two styli located in a block of similar size and position to block 100.

One advantage of the method of FIG. 8, whether optical, magnetic or mechanical indicia are used, is that higher sensing resolution is possible compared with the sensing resolution obtainable in the method of FIG. 2. The higher resolution permits a closer spacing of indicia, which is of particular advantage in sensing the speed of movement of the handpiece, and even allows a determination of whether the speed of movement is increasing or decreasing.

Regarding speed of movement of the handpiece, as discussed above, there are two primary criteria which may determine a maximum possible speed of movement for the handpiece. One of these criteria is the maximum possible firing rate of the laser, the other is the rate at which chilled lens 58 can adequately cool skin 48. Should the latter be the limiting criterion, the limitation can be overcome by pre-cooling an untreated sub-area of skin 48 while an adjacent sub-area of the skin is being treated. Referring to FIGS. 9–11, one preferred means of effecting such a pre-cooling is to provide a pre-cooling plate 104 of about the same area as, and adjacent to, lens 58 and about level with contact surface 59 thereof.

Pre-cooling plate 104 is preferably formed from a material having a high coefficient of thermal conductivity such as copper. If copper is selected, it is preferable that it be coated or plated with a hard corrosion-resistant material, for example, nickel or rhodium. In handpiece 32Y, pre-cooling plate 104 is completely cooled by attaching it in thermal contact with cooling jacket 62 (not visible in FIGS. 9–11). Those skilled in the art may devise other arrangements for cooling pre-cooling plate 104 without departing from the spirit and scope of the present invention. Provision of the pre-cooling plate reduces the amount of cooling which must be provided by chilled lens 58, and can thus permit a speed of movement up to the laser firing rate limit for apparatus 30.

Figure 12:
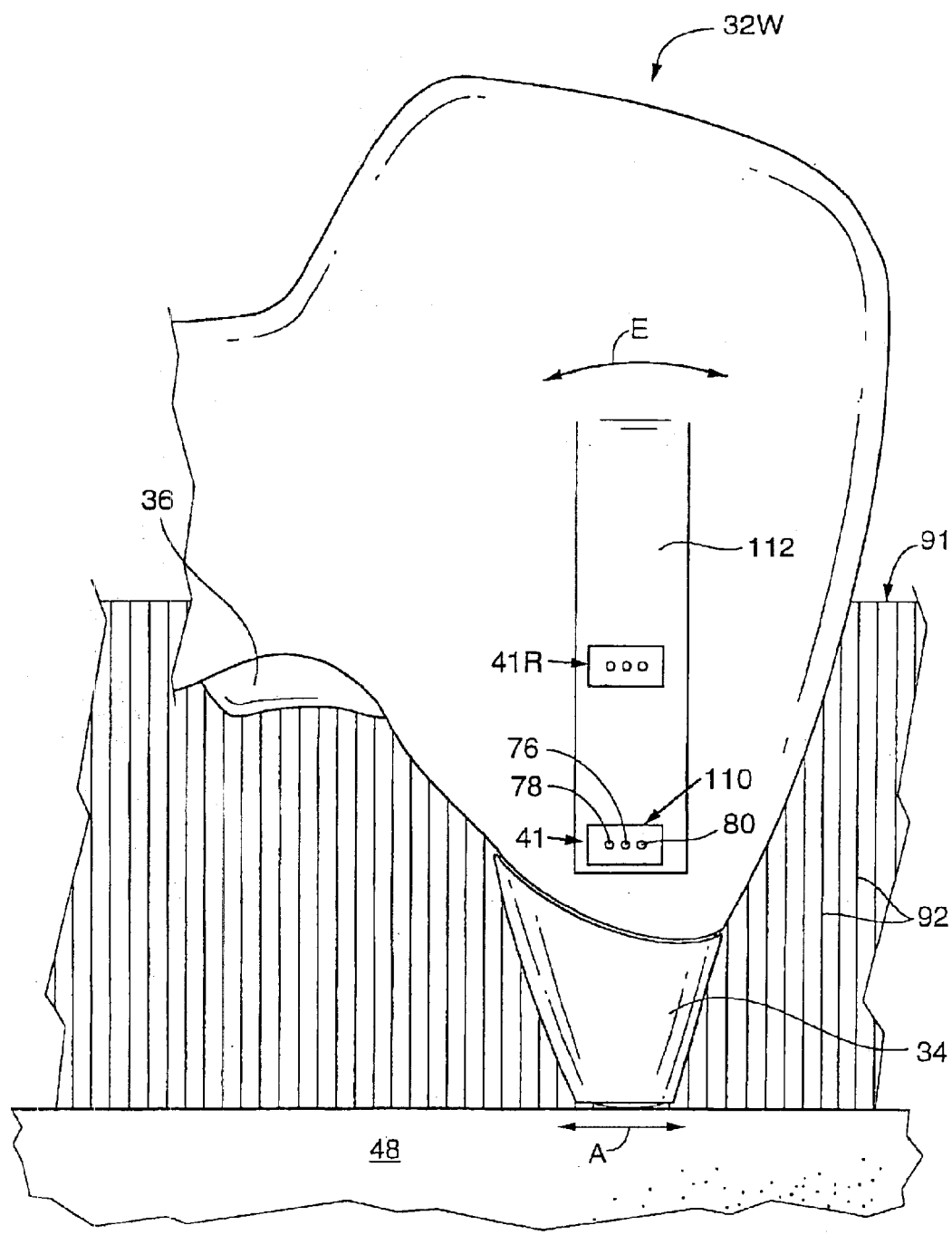
FIG. 12 is a partial side elevation view schematically illustrating a fourth handpiece in accordance with the present invention arranged for automatic firing by sensing crossings of lines on a ruled guide-strip placed on edge, rulings facing sideways, in contact with skin being treated.
Figure 13:
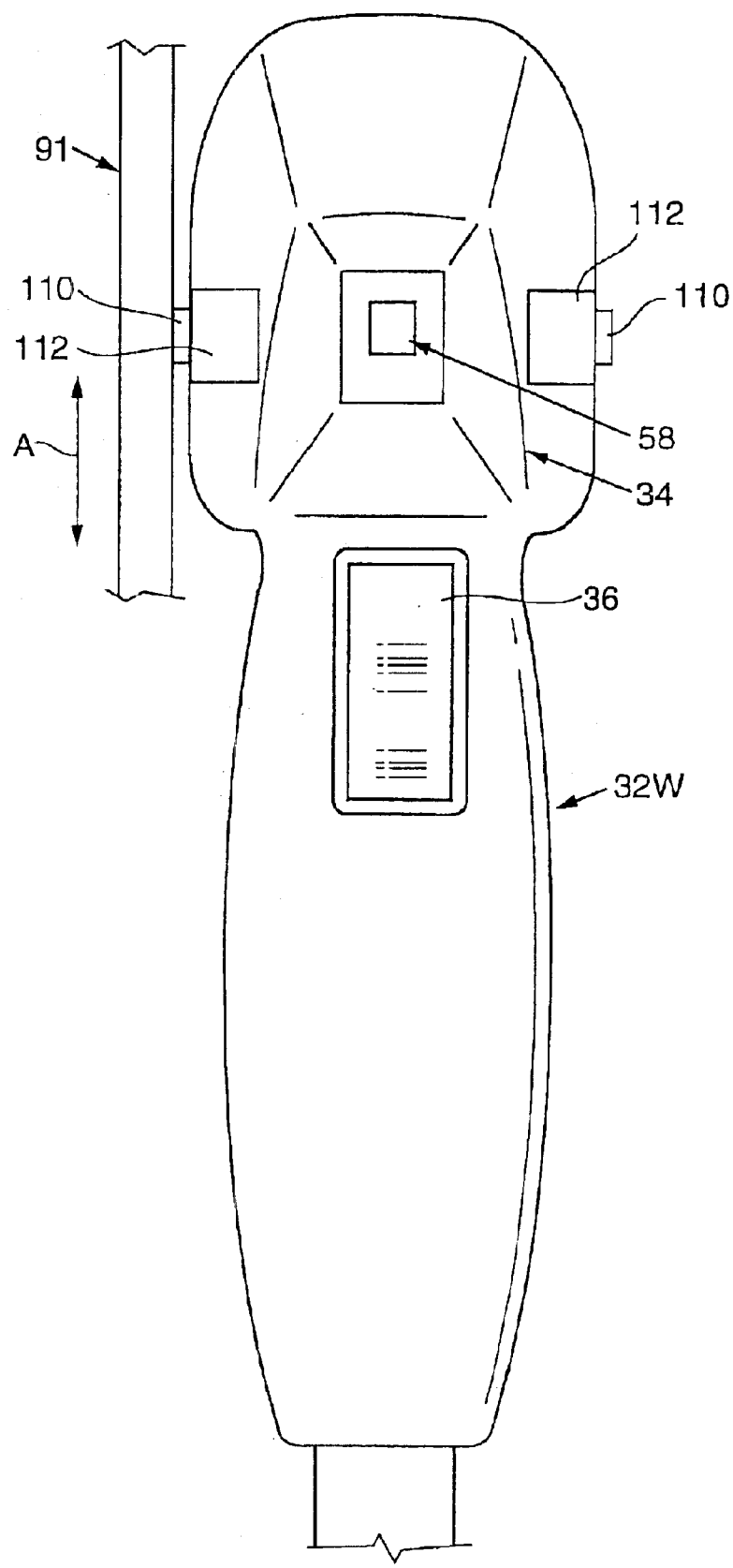
FIG. 13 is a front elevation view schematically illustrating further details of the handpiece of FIG. 12 including a side-looking position sensor for sensing the line-crossings.
Figure 14:
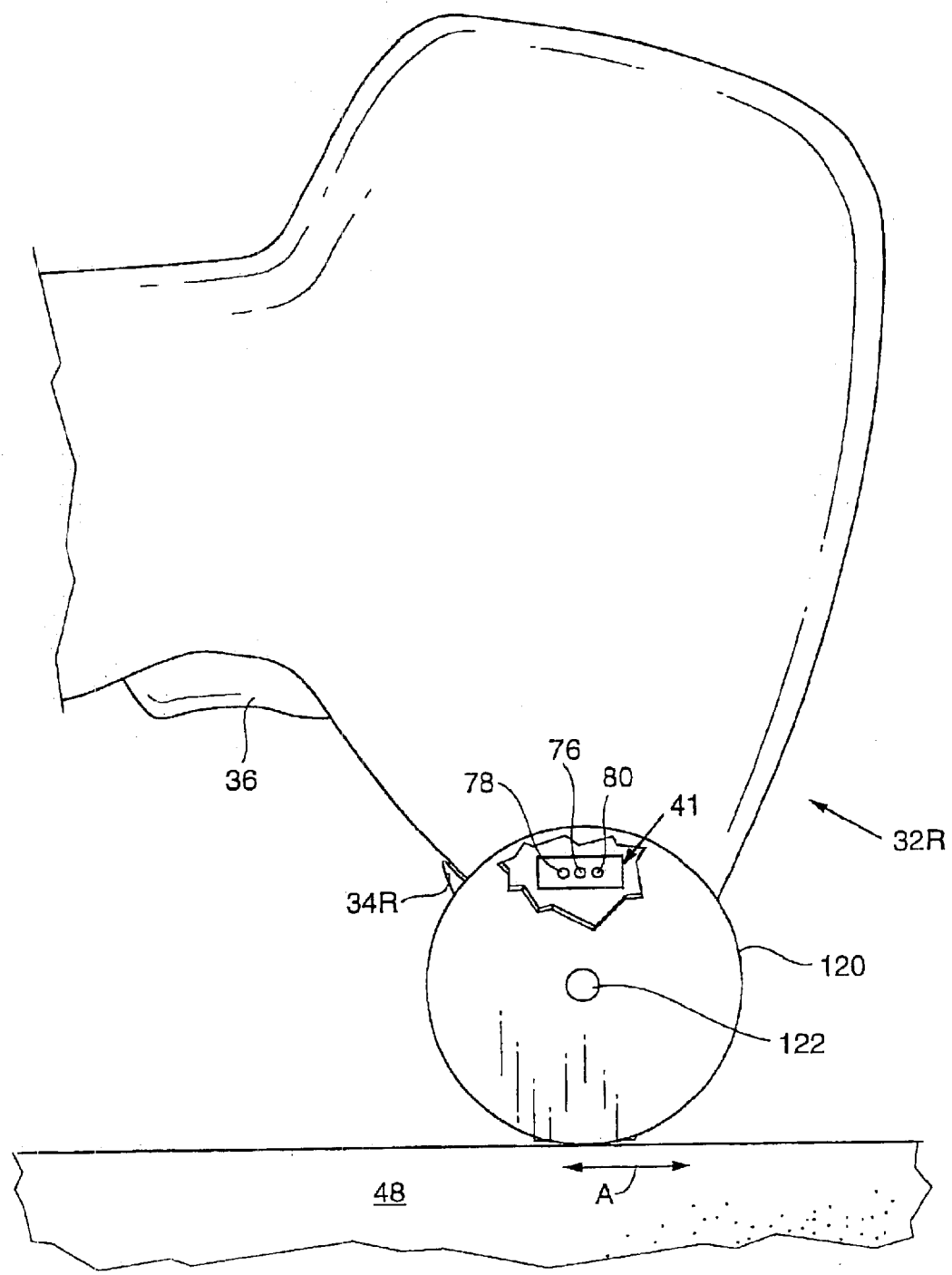
FIGS. 14 and 15 are partial side elevation views schematically illustrating opposite sides of a fifth handpiece in accordance with the present invention arranged for automatic firing by sensing crossings of radial lines on wheel attached thereto, the wheel arranged to contact skin being treated.
Figure 15:
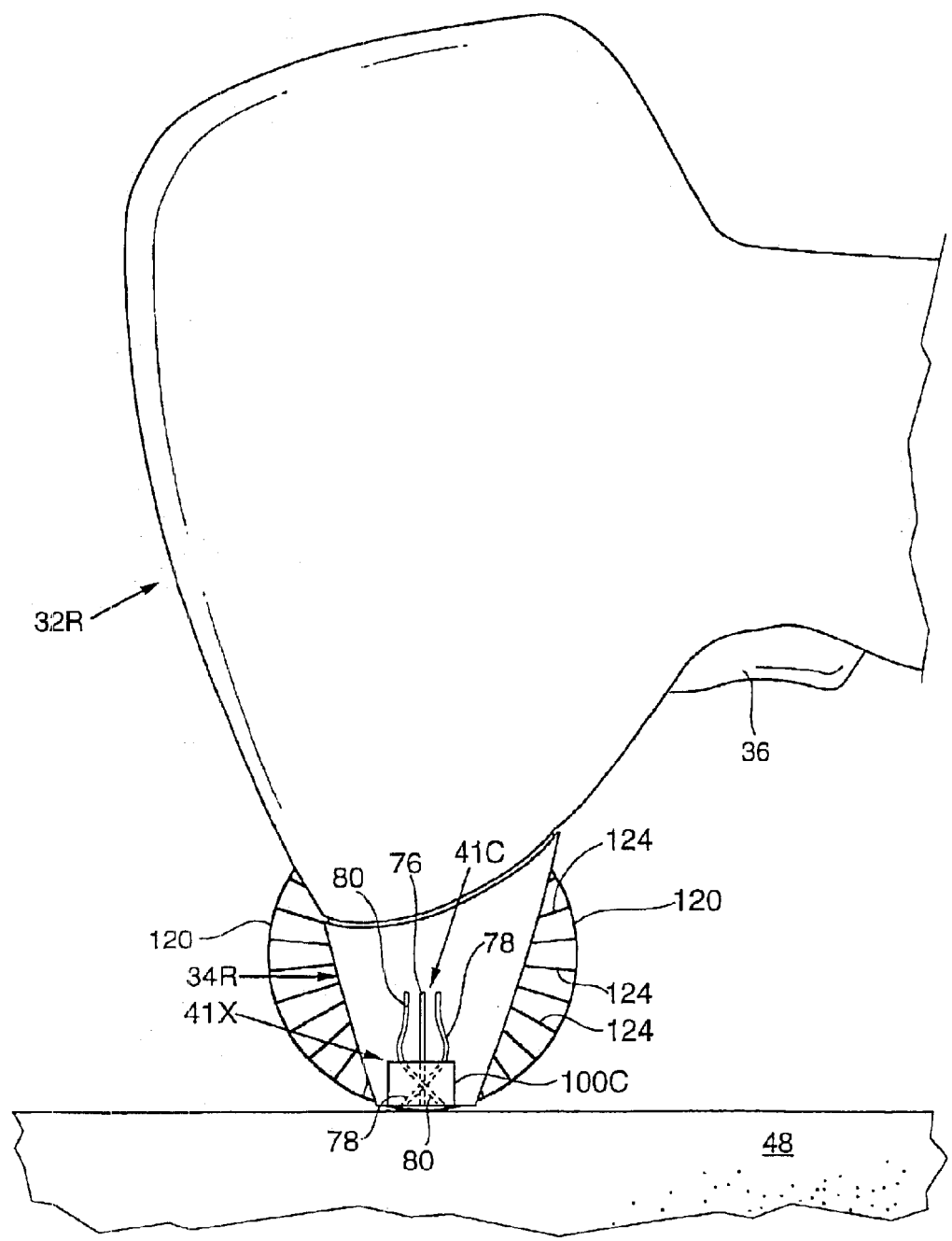
Figure 16:
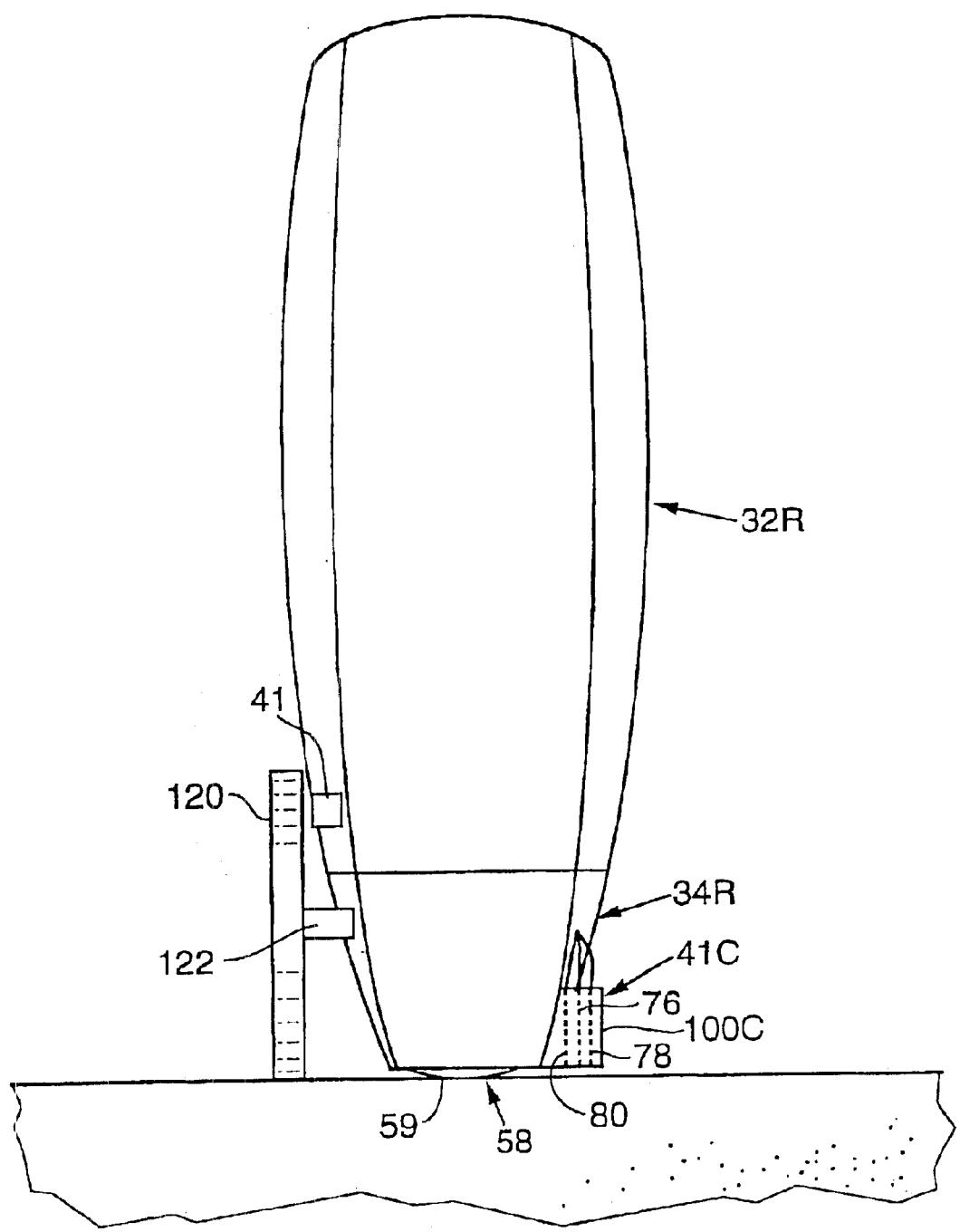
FIG. 16 is a plan view from above schematically illustrating further details of the handpiece of FIGS. 14 and 15.

Referring now to FIG. 12 and FIG. 13, still another automatic firing apparatus and method in accordance with the present invention includes placing a ruled guide strip 91, on edge, in contact with skin to be treated, and sensing crossings of rulings 92 thereon using a side-looking position sensor incorporated in a handpiece 32W in accordance with the present invention. The side-looking position sensor is similar to above-described sensor 41 with the exception that transmitting aperture 76 and receiving apertures 78 and 80 thereof face in a direction parallel to the plane of skin being treated. Apertures 76, 78 and 80 are located in block 110 attached to a lateral extension 112 of handpiece 32W.

In one preferred example of operation of handpiece 32, guide strip 91 is made from translucent material having opaque rulings 92, and handpiece 32W is moved, with sensor block 110 thereof in contact with guide-strip 93. Line-crossing detection occurs in the manner described above with respect to sensor 41 of handpiece 32. Alternatively, the guide-strip could be made of a reflecting material such as a metal and having a plurality of slots machined therein to define the rulings. In this case, a drop in detected light intensity would correspond to a line crossing.

Two position sensors with apertures thereof on opposite sides of handpiece 32W may be individually, selectively activated to provide for right or left hand operation of the handpiece as discussed above with reference to handpiece 32Y. Sensing methods are not limited to optical methods as described but may include magnetic and mechanical methods as discussed above.

A particular advantage of the guide strip arrangement of handpiece configuration of FIGS. 12 and 13 is that relative vertical motion (perpendicular to skin 48) between the handpiece and the guide strip is possible while still maintaining sensor apertures 76, 78 and 80 in contact with the ruled surface of the guide strip. This is particularly advantageous when treating skin of a strongly contoured body member such as a knee. Adding an additional sensor 41R on one or both sides of handpiece 32W (see FIG. 12) provides that rotary motion of the handpiece, in a direction indicated by arrows E, can be detected. This can provide an operator with a warning should the handpiece be inadvertently inclined in direction E to a degree which would compromise proper therapeutic treatment.

Referring now to FIG. 14, FIG. 15, FIGS. 15A–D and FIG. 16, another handpiece 32R in accordance with the present invention is configured for automatic firing without the need for a separate guide-strip or markings ruled on skin to be treated. Handpiece 32R includes a wheel or roller 120 which rotates about an axle 122 extending from tip 34R of the handpiece (see FIG. 14).

Roller 120 is arranged to make contact with skin 48 being treated when lens 58 of the handpiece makes contact with the skin. Moving the handpiece in the (longitudinal) direction indicated by arrows A causes roller 120 to rotate. Roller 120 includes radial markings or indicia 124 on the side thereof facing handpiece 32R. Indicia 124 have equal angular spacing. Handpiece 32R includes a position sensor 41 having side-looking apertures 76, 78 and 80 positioned to detect motion of indicia 124 in the manner described above in which similar sensors detect motion of a handpiece over fixed indicia.

The angular spacing of indicia 124 may be selected such that peripheral spacing of the indicia on roller 120 is equal to, or some sub-multiple of, the length of lens 58. Sensor 41 can thereby provide signals for automatic firing and speed of movement calculation as described above. Alternatively, the spacing may be reduced to the point where the line spacing is relatively small compared with the length of the lens, for example, about equal to a line width or less than that. In this case, with revolution of roller 120, sensor 41 generates a stream of signals similar to those generated by a conventional shaft encoder. This would allow automatic firing to be effected at any predetermined interval simply by correspondingly programming control electronics of console 38.

Preferably, rotary motion of roller 120 is damped such that the roller can not continue to rotate if contact thereof with skin 48 is lost. This provides that signals from sensor 41 can be used to determine loss of contact of handpiece 32R with skin 48. As an alternative or backup, however, another sensor 41C (see FIGS. 15, FIG. 15A, FIG. 15B, 15C and 16) can be provided, the purpose of which is only to sense contact, or loss thereof, with skin 48.

Contact sensor 41C is similar to above described position sensor 41 except for the arrangement of light delivery optical fiber 76 and light receiving fibers 78 and 80 in a block 100C (see FIGS. 15A–B for details) for holding the ends of the optical fibers in alignment with each other. In block 100C the relative angle between the fibers is about the same as for those of above-described sensor 41 but with the angular subtense diverging at the distal ends of the fibers rather than converging. This is achieved by crossing the receiving fibers 78 and 80 in-block 100C and arranging transmitting fiber 76 to bisect the angle between the receiving fibers.

A result of this arrangement is that the amount of scattered light received by the receiving fibers is somewhat reduced compared with the arrangement of sensor 41. The possibility of receiving fibers 78 and 80 receiving light from optical fiber 76 by any optical mechanism other than volume scatter through skin 48 is essentially eliminated. Because of this, the effectiveness of sensor 41C as a skin-contact sensor is increased compared with that of sensor 41.

Referring to FIG. 15C, where this arrangement functions as a skin-contact sensor only, it is possible to use a sensor block 100D which includes only a sending fiber 76 and a receiving fiber 78. This allows a greater angular divergence between the sending and receiving fibers. In FIG. 15D is schematically depicted the output of a detector cooperative with a sensor head 100D when the sensor head (the distal tips of fibers 76 and 78) is at distances of between 0.0 and 3.0 mm from surfaces of opaque grey plastic (curve F) light-colored skin (curve G) and translucent white plastic (curve H). About 0.5 milliwatts (mW) of light at a wavelength of about 660 nm is delivered from optical fiber 76. Optical fibers 76 and 78 each have a diameter of 1.0 mm and are inclined at 40° from vertical, i.e., with an angle of 80° therebetween. The tips of the optical fibers are laterally and longitudinally separated by 2.0 mm. It can be seen that there is essentially zero detector output from the opaque grey plastic surface at any distance up to contact. A similar result was obtained on a rough (diffusely reflecting) steel surface.

For skin (skin of a finger in this experiment) and translucent plastic, output increases gradually as the sensor approaches the surfaces. Applying a force of 10.0 grams (g) to the sensor head on the skin surface caused the detector output to rise sharply from about 18.0 to 29.5, indicating the effectiveness of the sensor head as a contact sensor. A further increase in force provided no significant increase in output. In practice, a threshold level of detection can be set at the detector output level at skin contact. It is a relatively simple matter to provide a calibration capability, via a potentiometer or the like, to adjust the threshold for different skin shades. Contact of the sensor head, or lack thereof, can then be determined according to whether the detector output is above or below the set threshold level.

Figure 17:
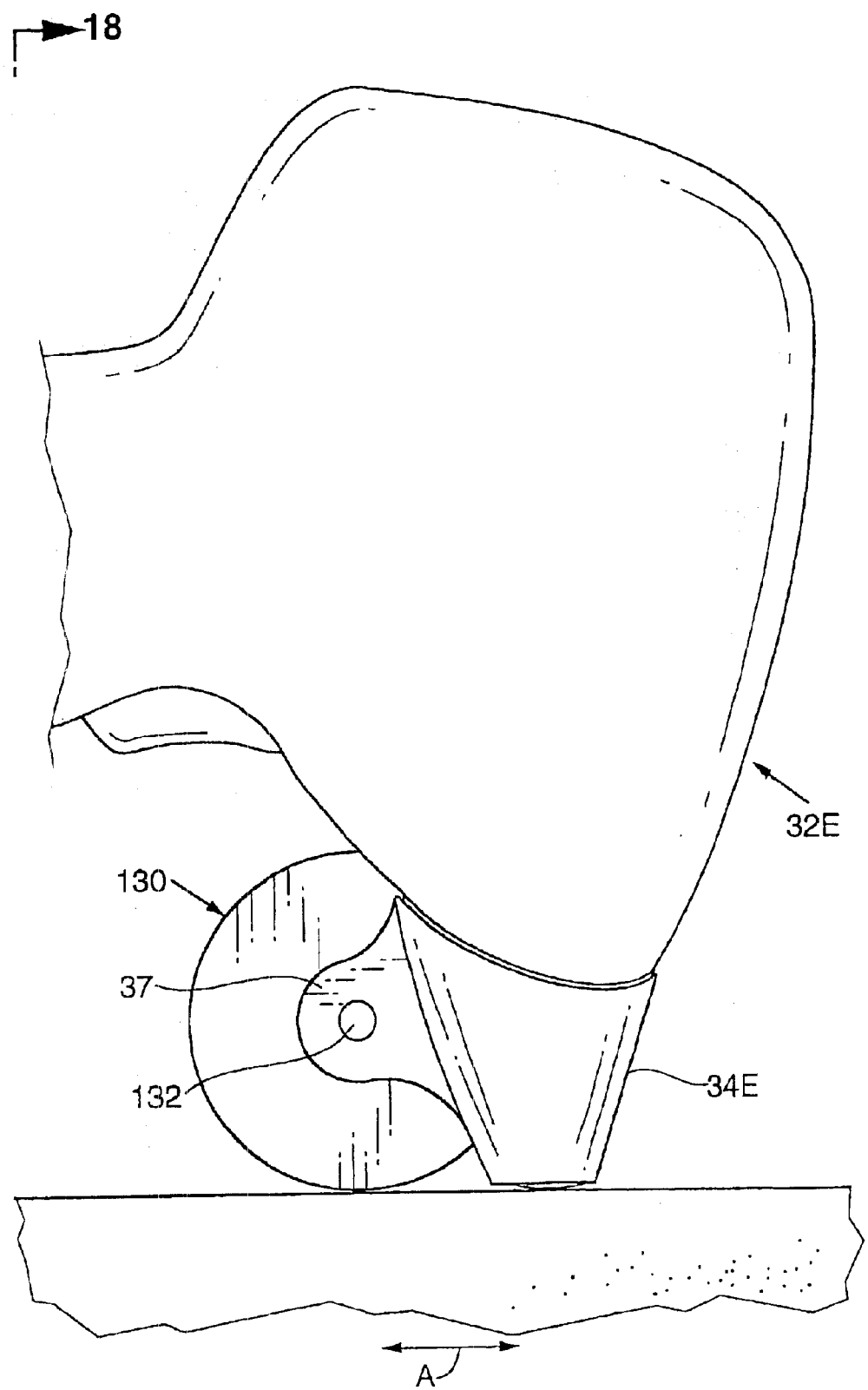
FIG. 17 is a partial side elevation view schematically illustrating opposite sides of a sixth handpiece in accordance with the present invention having a wheel attached thereto and connected to a shaft encoder, the wheel arranged to contact skin being treated and the handpiece arranged for automatic firing responsive to signals provided by the shaft encoder.
Figure 18:
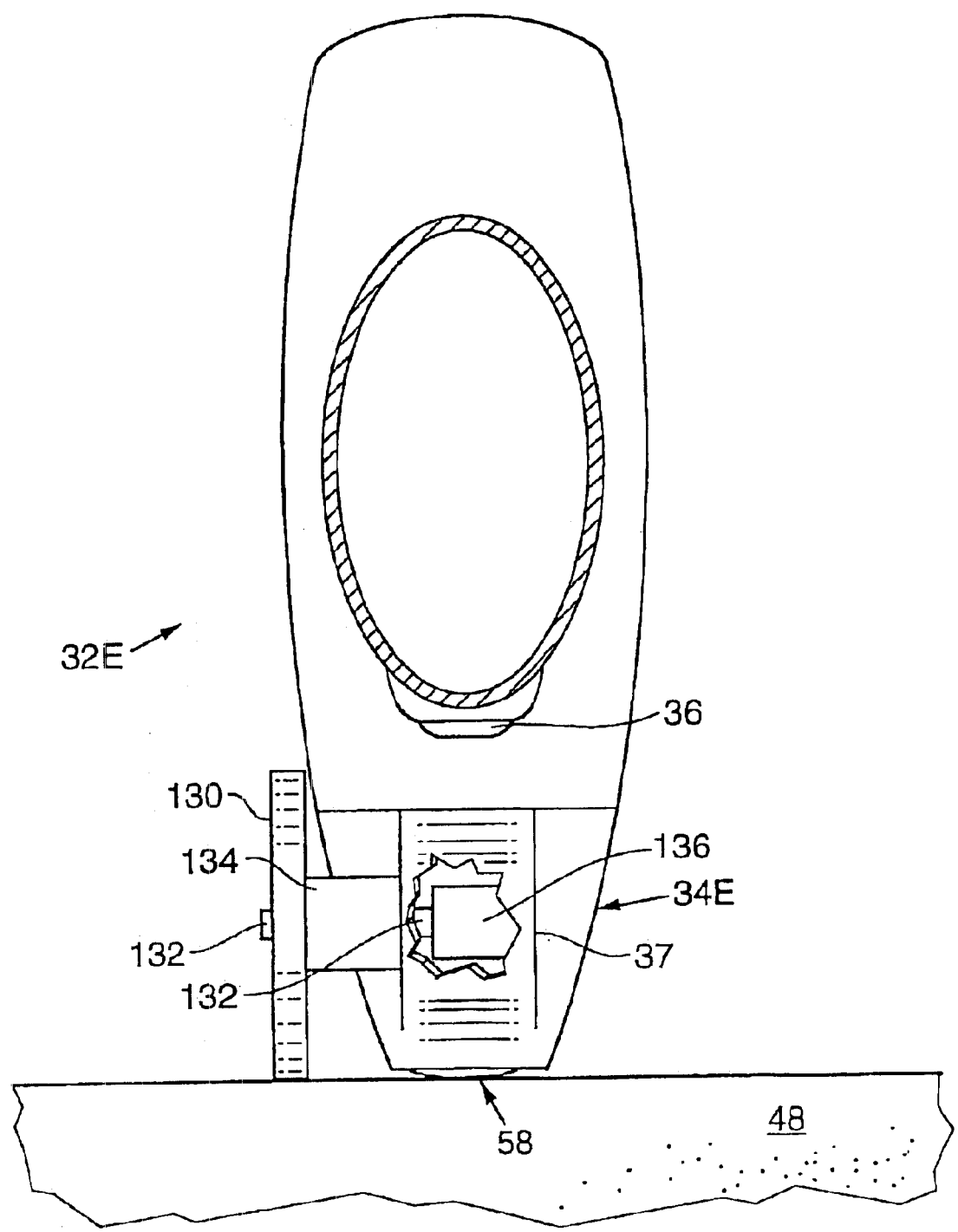
FIG. 18 is a plan view of the handpiece of FIG. 17 seen generally in the direction 18—18 of FIG. 17 and schematically illustrating further details of the wheel and a shaft-encoder and bearing housing on the tip of the handpiece.

Referring now to FIG. 17 and FIG. 18, another handpiece 32E in accordance with the present invention includes a wheel or roller 130. Roller 130 is rotatable on an axle 132 which extends through a bearing housing 134 into an extended portion 37 of tip 34E of handpiece 32E. Axle 132 engages a shaft encoder 136 located in extended portion 37 of tip 34E.

Roller 130 is arranged to make contact with skin 48 being treated when lens 58 of the handpiece makes contact with the skin. Moving the handpiece in the (longitudinal) direction indicated by arrows A causes roller 130 to rotate. Rotation of roller 130 is monitored by shaft encoder 136. Signals from shaft encoder 136 representative of the angular position or degree of rotation of roller 130 are transmitted to control electronics in control console 38 (see FIG. 1) and used for triggering automatic firing and computing speed of motion of the roller. Making or breaking contact with skin 48 by tip 34E of handpiece 32E can be detected by the control electronics detecting respectively initiation and termination of rotation of roller 130 via signals from shaft encoder 136. Alternatively or additionally, an optical skin contact sensor of the type described above with reference to handpiece 32R may be provided.

Figure 19:
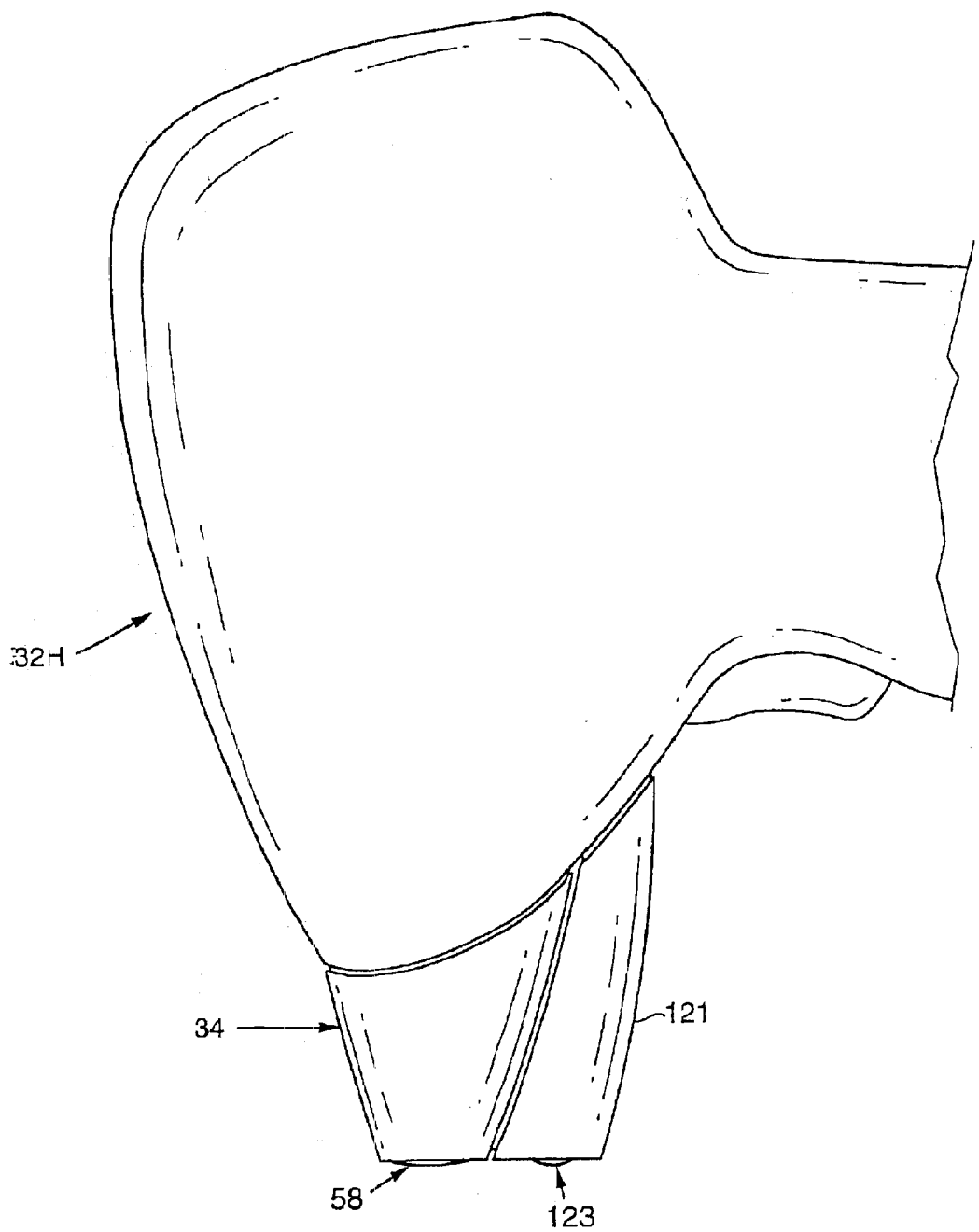
FIG. 19 a side elevation view schematically illustrating a ninth handpiece in accordance with the present invention, having a detachable housing including a roller cooperative with a position sensor.
Figure 20:
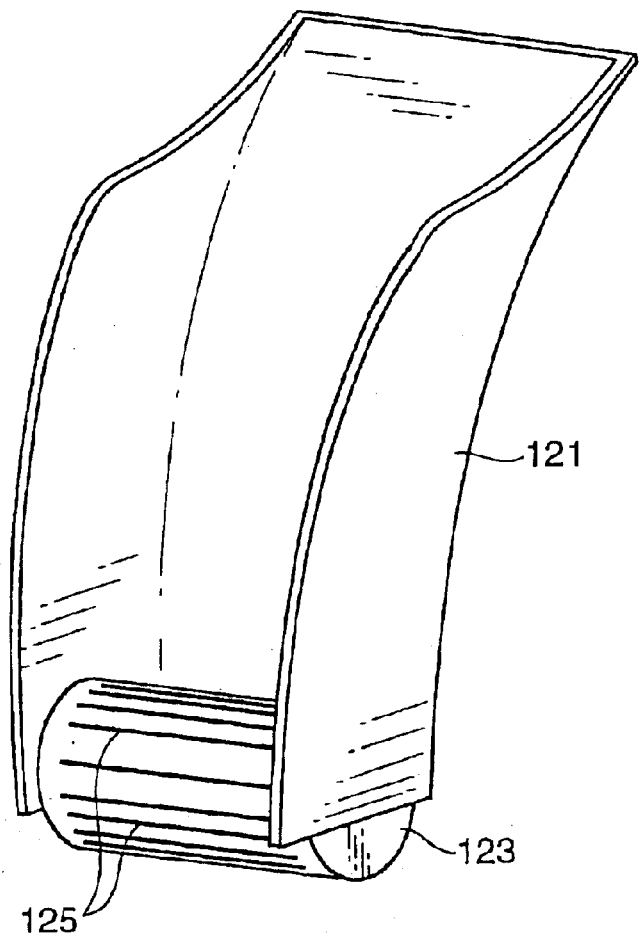
FIG. 20 is a perspective view schematically illustrating the detachable housing and roller of FIG. 19.
Figure 21:
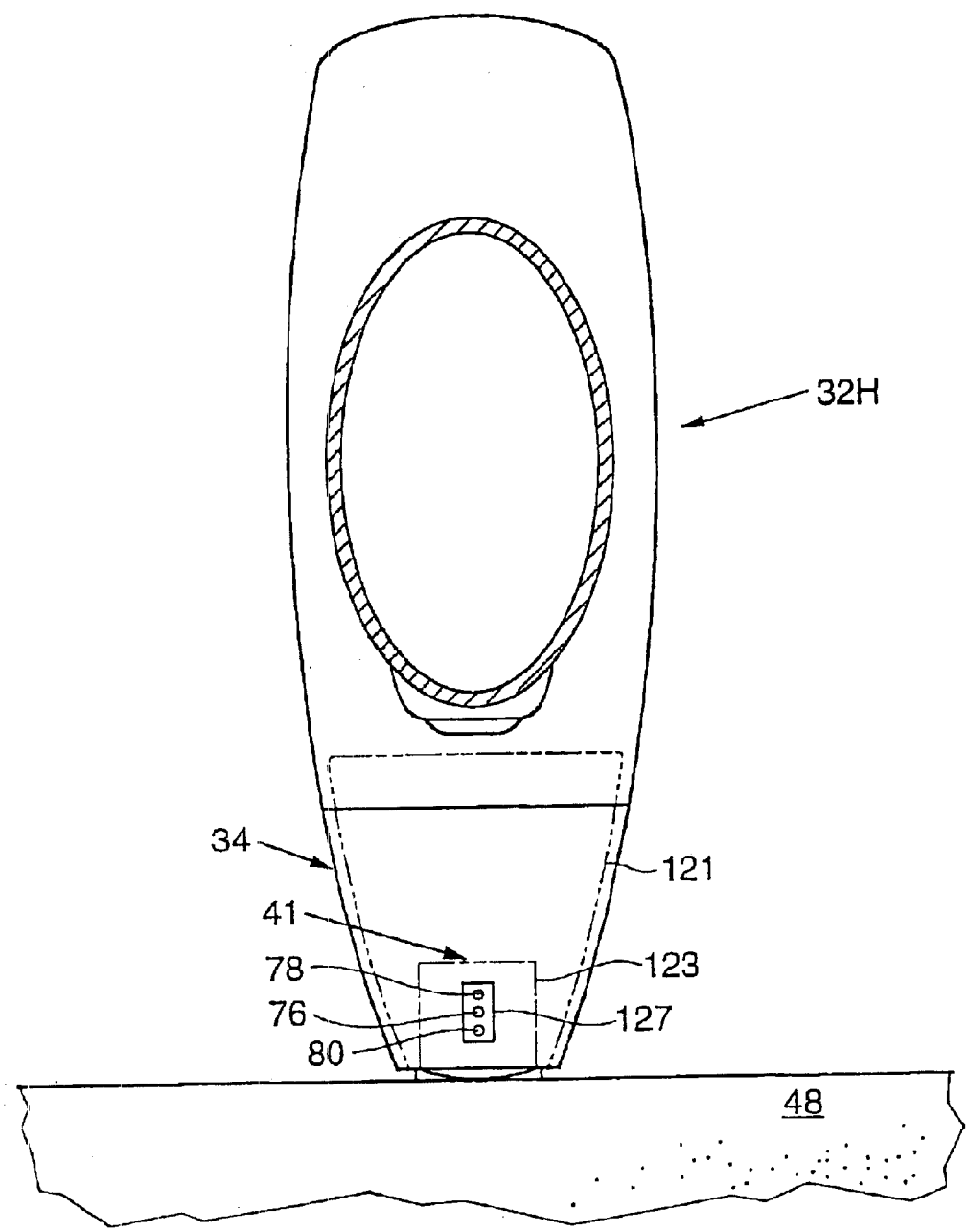
FIG. 21 is a plan view from below schematically illustrating the handpiece of FIG. 19 without the detachable housing and showing a vertically-oriented position sensor head for sensing rotation of the roller of FIG. 20.

Referring now to FIG. 19, FIG. 20 and FIG. 21, another handpiece 32H in accordance with the present invention is illustrated. Handpiece 32H includes a detachable housing 121 (shown in phantom in FIG. 21) which attaches to tip 34 of the handpiece. Detachable housing 121 includes a wheel or roller 123 arranged to engage skin 48 being treated when lens 58 of tip 34 is placed in contact with the skin.

Roller 123 includes a series of equally-spaced, parallel (paraxial) longitudinal rulings 125 around a cylindrical surface of the roller (see FIG. 20). The spacing of the rulings is preferably equal to or some sub-multiple of the length of lens 58 for reasons discussed-above, for example, with reference to handpiece 32R. Alternatively the lines may be set sufficiently close together that the roller and detector function in the manner of a conventional shaft encoder as discussed above.

A sensor block 127 including distal ends of optical fibers 76, 78 and 80 of a position sensor 41 is located on tip 34 of handpiece 32H (see FIG. 21). Here, the distal ends of the fibers are arranged in a vertically-oriented line such that the position sensor can detect the passage of rulings 125 of roller 123 as the roller rotates responsive to motion of the handpiece over skin 48. From the detection of rulings, the position of handpiece 32H on skin 48 can be determined as discussed above.

Figure 20A:
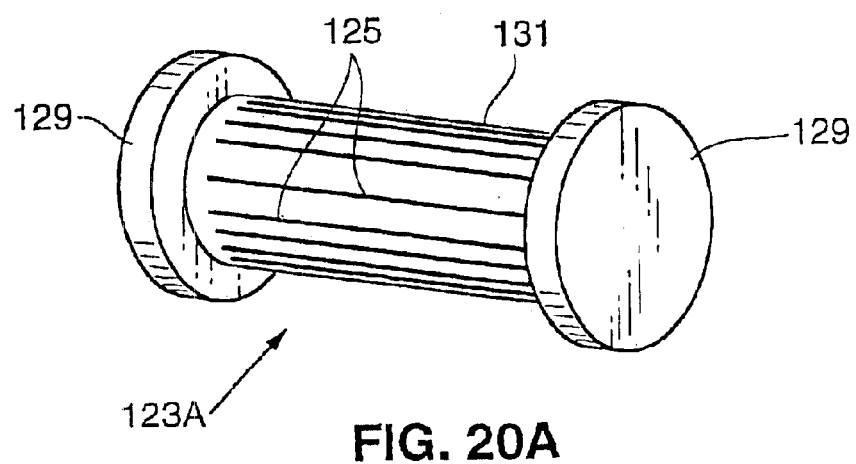
FIG. 20A is a perspective view schematically is illustrating an alternative form of roller for the handpiece of FIG. 19.

Referring to FIG. 20A, an alternative roller 123A for handpiece 32H is illustrated. Roller 123A comprises two coaxial cylindrical portions 129 and bounding a cylindrical portion 127 coaxial therewith but having a lesser diameter than cylindrical portions 129. Here, paraxial rulings 125 are made on cylindrical portion 127. This helps minimize contact with the rulings on contacting skin 48 when roller 123A contacts skin 48 via cylindrical portions 129 thereof. Contact of rulings 125 with skin 48 could progressively lead to contamination with skin grease, skin debris and the like.

Such contamination could lead to errors in the accuracy of position determination by position sensor 41.

Handpiece 32H is described above as including a position sensor 41 having a light-source and detectors thereof located in the body of the handpiece and connected to a sensor block by optical fibers. Those skilled in the art will recognize however that a similarly functioning sensor head could be positioned in detachable housing 121 without departing from the spirit and scope of the present invention. In fact it is possible to locate all components of a position detector in detachable housing 121, requiring only an electrical connection with the body of the handpiece for power and data communication.

It is pointed out here that indicia on any above-described rollers may be dark lines on a bright background or bright lines on a dark background. Alternatively, the indicia may be fluorescent, or may be magnetic if sensor 41 is replaced with a magnetic pick-up arrangement.

Figure 22:
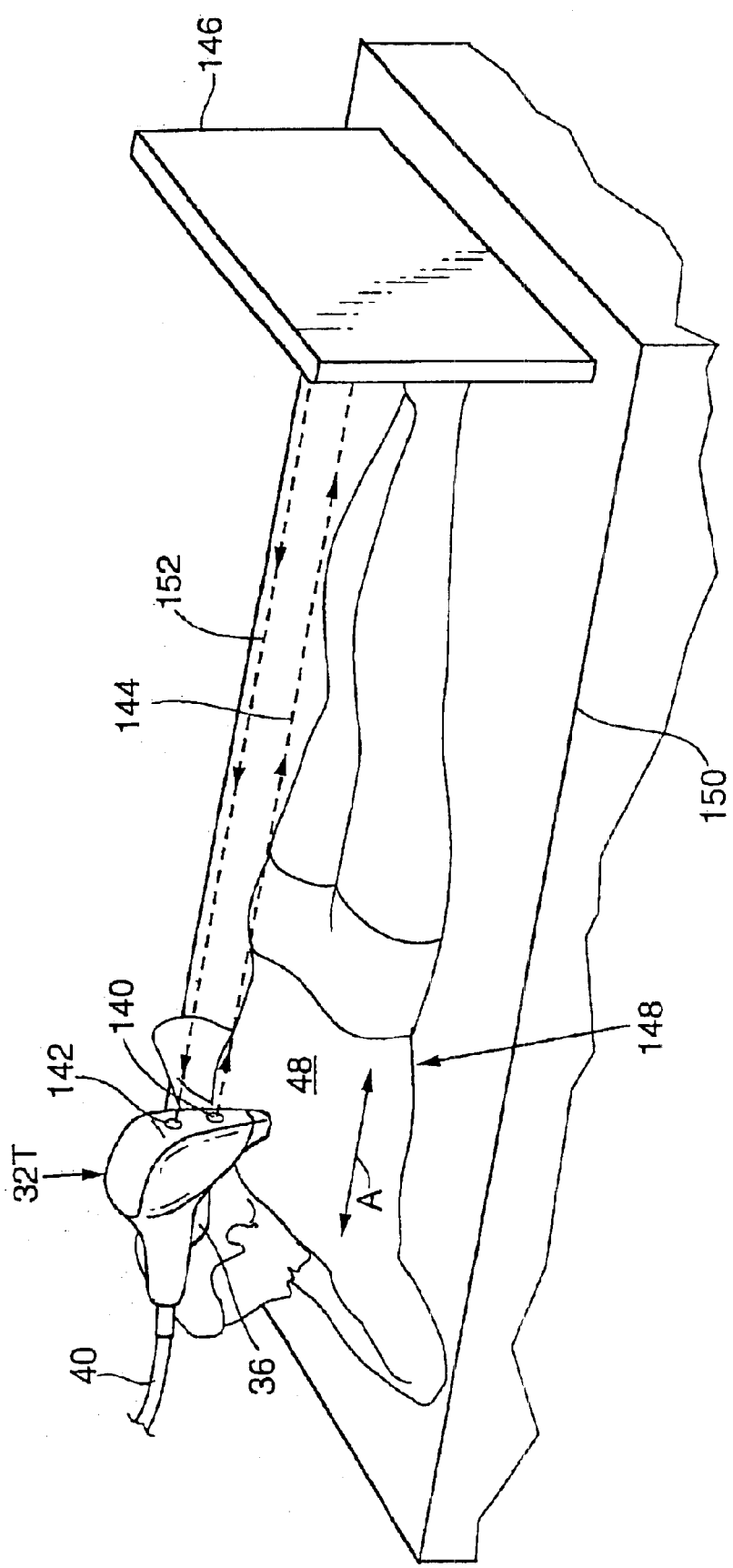
FIG. 22 is a perspective view schematically illustrating a seventh handpiece in accordance with present invention, including a transponder, for sending a signal to a screen located proximate a patient being treated, and a receiver for receiving an echo of the signal from the screen for determining the position of the handpiece in one dimension relative to the patient.

Referring now to FIG. 22, another handpiece 32T in accordance with the present invention includes a transponder 140 and a receiver 142. Preferably, transponder 140 is an ultrasonic emitter and receiver 142 is an ultrasonic detector. Transponder 140 sends a signal-pulse (dashed line 144) to a screen or wall 146 located proximate a patient 148 on whose back skin 48 is being treated. Here, screen 146 is shown mounted on a table 150 on which patient 148 is lying in a face-down position.

Receiver 142 receives an echo (a return-pulse) of the signal-pulse sent by transponder 140 (dashed line 152) from screen 146. Control electronics of console 38, connected to transducer 140 and receiver 142 record the time of sending signal-pulse 144 and time of receiving echo 152 corresponding thereto and determine a time difference between the sending and receiving. The time difference between the sending of signal-pulse 144 and the receiving of echo 152 provides a measure of the position of handpiece 32T with respect to screen 146 and, accordingly, with respect to patient 148 as the handpiece is moved in a longitudinal direction indicted by arrows A. These position measurements are used by control electronics of console 38 to automatically trigger firing of the laser at equal position increments of handpiece 32T, and, optionally, to monitor the speed of motion of handpiece 32T as discussed above with reference to other embodiments of the apparatus and method of the present invention.

It should be noted here that the treatment illustrated in FIG. 22 and the position of screen 146 with respect to patient 148 are merely exemplary. Those skilled in the art may devise other screen locations adapted to other treatments without departing from the spirit and scope of the present invention.

It should also be noted that while an ultrasonic emitter and receivers are preferred in the above described embodiment of the present invention, the operating principles of this embodiment are applicable if transponder 140 (and corresponding receiver 142) rely on sending and detection of signals other than ultrasonic signals. By way of example, these may be optical signals (pulses) generated by a laser, forming in effect a laser rangefinder. The laser may be located in, or on, handpiece 32T, or may be remote therefrom with radiation from the laser being delivered to transponder 140 by an optical fiber. The signals may also be radar signals (pulses) with transponder 140 being a miniature, (for example incorporated in a semiconductor chip) radar transmitter. In the case of optical or radar signals, electronic processing of the signals may prove to be more complex than for ultrasonic signals, because of the relatively short distances traversed by signal pulses and, correspondingly, the relatively very short time between sending and detection thereof.

Figure 23:
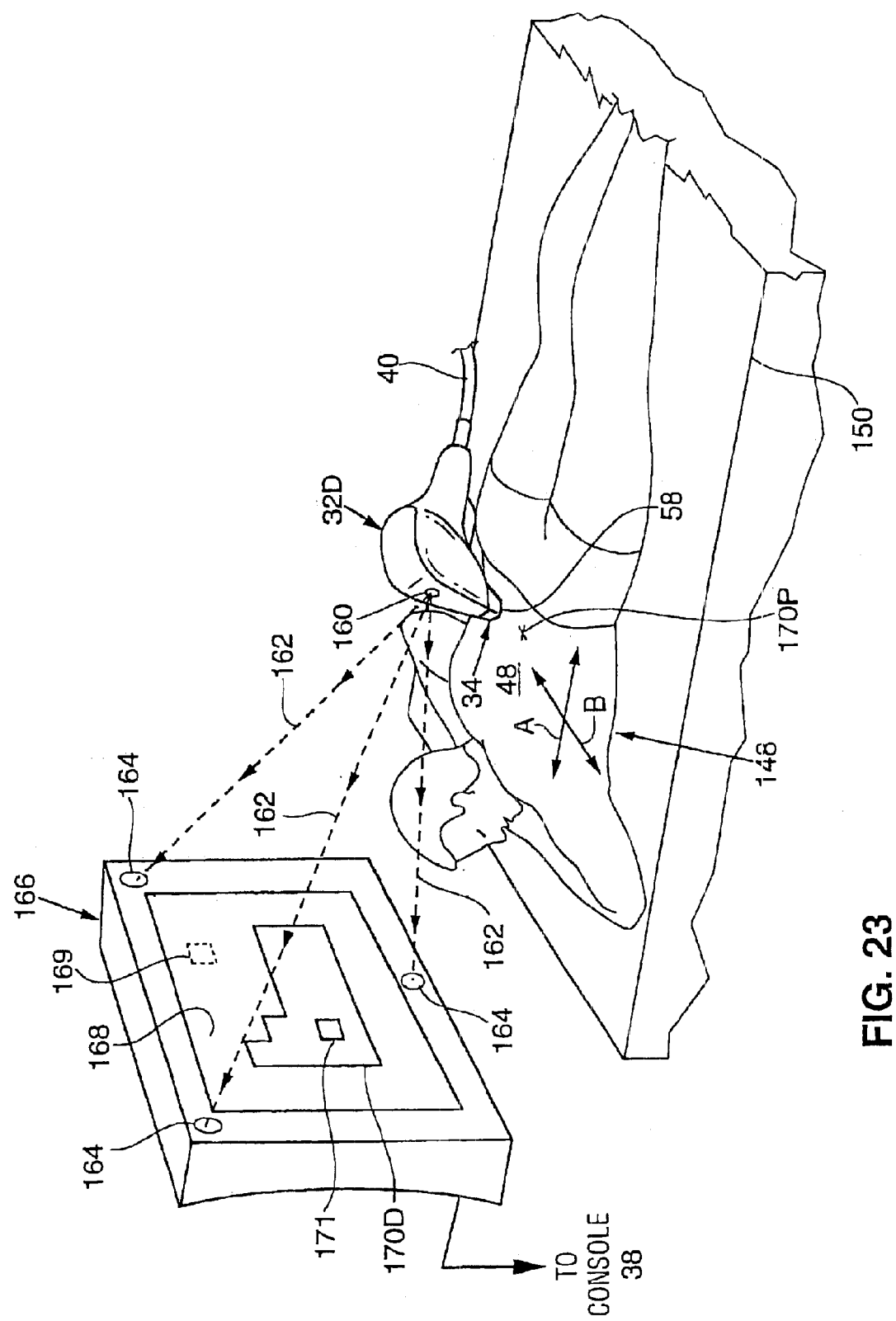
FIG. 23 is a perspective view schematically illustrating an eighth handpiece in accordance with present invention, including a transponder for sending a signal to three direction sensitive detectors proximate a patient being treated, signals from the detectors being used for determining the position of the handpiece in at least two dimensions relative to the patient.

Referring now to FIG. 23, another handpiece 32D in accordance with the present invention includes a transponder 160. Preferably, transponder 160 is an ultrasonic emitter. Transponder 160 sends a signal-pulse (dashed lines 162) radiating therefrom in a diverging manner to three receivers 164, preferably ultrasonic detectors incorporated in a video display unit (VDU) 166 having a display 168. Here, VDU 166 is shown positioned proximate table 150 on which patient 148, on whose back skin 48 is being treated, is lying in a face-down position.

In one example of signal processing for the arrangement of handpiece 32D and receivers associated therewith, for each signal-pulse the difference in arrival time at each the receivers is recorded. Based on this difference in arrival time, and on the spacing of the receivers, control electronics associated with the transponder and receivers determine, by triangulation, a position in longitudinal direction A and lateral direction B for transponder 160 relative to a plane in which the receivers are located. Here the plane is of the front of VDU 166. This position measurement is used by control electronics of console 38 to automatically trigger firing of the laser depending on its lateral and longitudinal position. A visual record of the firings is presented on display 168.

It should be noted here that, in theory at least, only two detectors are necessary to provide two dimensional position location for the handpiece. Providing three detectors can increase the accuracy of two dimensional position location and also provide information on position in a third (perpendicular to the general plane of the skin) direction. This information can be useful if a contoured area of skin, for example, a knee, is being treated.

In one example of operation of handpiece 32D, point 170P on patient 148 designates the lower left-hand corner (origin) of an area of skin 48 to be treated. This area is considered to be divided into a series on sub-areas equal in dimension to lens 58 of handpiece 32D. Point 170D on display 168 is electronically arranged to represent point 170P on patient 48.

The instantaneous position of handpiece 32D relative to point 170P is indicated on display 168 by a square "cursor" 169 having dimensions representing the area treatable in a single firing of the laser. Treatment is initiated by placing tip 34 of handpiece 32D in contact with skin 48 of patient 148 and activating trigger 36 of the handpiece to begin automatic firing.

Each successful firing is recorded on display 168 as a solid square, thereby providing a direct indication of progress of the treatment and of any areas such as an area 171 which may have been "missed". Control electronics may also be arranged to store an electronic map of successful firings. The stored electronic map can be used by the control electronics to automatically fire the laser when the position detection system senses that the handpiece tip is contacting the skin in a missed area. The stored electronic map can also be used by the control electronics to prevent manual firing of the laser if the handpiece tip is in contact with the skin in an area that has already been successfully treated.

It should be noted here that receivers 164 are shown integrated into VDU 166 as one convenient location for the detectors. Receivers 164 may also be located remote from VDU 166 and supported on a separate frame and locations may be varied according a specific treatment. Such locations may be selected and varied without departing from the spirit and scope of the present invention.

While preferred embodiments of the present invention are described above with reference to tracking motion of a handpiece in which a laser source is located, the present invention is not limited to use with such a handpiece. Principles of the application are also applicable to a handpiece which delivers radiation received from a remotely located source of laser-radiation. Such a handpiece, for example, may receive radiation from the remote source via an optical fiber or bundle of optical fibers or via a hollow articulated arm. Further, principles of the present invention are equally applicable if treatment does not require that the tip or delivery aperture of the handpiece is in contact with skin being treated. By way of example, the tip may include a lens for shaping or focussing the delivered radiation and may be spaced at a relatively short distance (about one or two centimeters) from the skin with spacing being maintained by an open jig in contact with the skin.

It should also be noted that automatic firing in accordance with the present invention has been described with reference to controlling firing such that sub-areas treated in a single firing are "tiled" together more or less contiguously to cover a total area to be treated, any of the above described embodiments to covering an area by overlapping treated sub-areas in a predetermined pattern. By way of example, each treated (in a single firing) sub-area may overlap the previously treated sub-area by half the length of the sub-area. This may be done for example to avoid the possibility of any narrow untreated areas being left between treated sub-areas.

Generally, the present invention is described and depicted herein in terms of a preferred and other embodiments. The invention, however, is not limited by those embodiments described and depicted. Rather, the invention is limited only by the claims appended hereto.

What is claimed is:

1. A method of treating an area of skin with a laser by delivering a series of laser-radiation pulses to the skin, each of the laser pulses treating a sub-area of the area to be treated, the method comprising the steps of:
   (a) providing a laser which, on being fired, generates a pulse of laser-radiation;
   (b) providing a handpiece for delivering a pulse of laser-radiation from said laser to the skin being treated;
   (c) providing a plurality of regularly spaced indicia on or adjacent the area of skin being treated;
   (d) while moving the handpiece over the skin being treated, electronically determining at least from said indicia the location of said handpiece in the area of skin being treated; and
   (e) automatically firing the laser when said electronically determined location corresponds to a sub-area to be treated.

2. A method of treating an area of skin with a laser by delivering a series of laser-radiation pulses to the skin, each of the laser pulses treating a sub-area of the area to be treated, the method comprising the steps of:
   (a) providing a laser which, on being fired, generates a pulse of laser-radiation;
   (b) providing a handpiece for delivering a pulse of laser-radiation from said laser to the skin being treated;
   (c) while moving the handpiece over the skin being treated, electronically determining the location of said handpiece in the area of skin being treated wherein said location determining further comprises the steps of (i) providing a plurality of regularly spaced indicia on or adjacent the area of skin being treated (ii) providing at least one sensor on the handpiece said sensor arranged to detect passage of the handpiece by one or more of said indicia as the handpiece is moved over the skin being treated;
   (d) automatically firing the laser when said electronically determined location corresponds to a sub-area to be treated wherein said automatic firing is triggered by the passage of the handpiece by one or more of said indicia.

3. The method of claim 2 wherein said indicia are spaced apart by a distance equal to one of a linear dimension of the sub-area, irradiated by said laser pulse; a distance equal to a sub-multiple of a linear dimension of the sub-area irradiated by said laser pulse; and a distance relatively small compared with a linear dimension of the sub-area irradiated by said laser pulse.

4. The method of claim 2, wherein said indicia are one of graphic indicia, magnetic indicia, and mechanical indicia.

5. The method of claim 4, wherein said indicia are magnetic indicia.

6. The method of claim 4, wherein said indicia are mechanical indicia.

7. The method of claim 4, wherein said indicia are graphic indicia.

8. The method of claim 7, wherein said sensor includes a light-source arranged to direct light onto the skin being treated such that the thus directed light is scattered by the skin being treated; wherein said sensor includes one or more light detectors arranged to detect said scattered light; wherein said graphic indicia are equally-spaced parallel lines drawn on the area of skin being treated in a medium which is at least partially opaque to the wavelength of light emitted by said light-source and adequately transparent to the wavelength of said pulse of laser radiation to enable desired treatment through said medium; and wherein passage of the handpiece by any one of said indicia results in a reduction in said scattered light detected by said at least one detector, said reduction in scattered light indicating that one of said indicia has been passed.

9. The method of claim 7, wherein said graphic indicia are equally-spaced parallel lines drawn on a strip of material placed on or adjacent to the area of skin being treated; wherein said sensor includes a light-source arranged to direct light onto the strip such that the thus directed light is scattered by the strip; wherein said sensor includes one or more light detectors arranged to detect said scattered light; wherein said strip is diffusely reflective at the wavelength of light emitted by said light-source for said directed light and said lines are drawn in a medium which is absorbent at the wavelength of light emitted by said light-source; and wherein passage of the handpiece by any one of said indicia results in a reduction in said scattered light detected by said at least one detector, said reduction in scattered light indicating that one of said indicia has been passes.

10. The method of claim 7, wherein said graphic indicia are equally-spaced parallel lines drawn on a strip of material placed on or adjacent to the area of skin being treated; wherein said sensor includes a light-source arranged to direct light onto the strip; wherein said strip is absorbent at the wavelength of light emitted by said light-source and said lines are drawn in a medium which is diffusely reflective at the wavelength of light emitted by said light-source; wherein said sensor includes one or more light detectors arranged to detect directed light diffusely reflected by said lines; and wherein passage of the handpiece by any one of said indicia results in an increase in light detected by said at least one detector, said increase in detected light indicating that one of said indicia has been passed.

11. The method of claim 7, wherein said graphic indicia are equally-spaced parallel lines drawn on a strip of material placed on or adjacent to the area of skin treated; wherein said sensor includes a light-source arranged to direct light onto the strip; wherein said lines are drawn in a medium which is fluorescent on irradiation with light emitted by said light-source; wherein said sensor includes one or more light detectors arranged to said fluorescence; and wherein passage of the handpiece by any of said indicia results in increase in light detected by said at least one detector, said increase in detected light indicating that one of said indicia has been passed.

12. A method of treating an area of skin with a laser by delivering a series of laser-radiation pulses to the skin, each of the laser pulses treating a sub-area of the area to be treated, the method comprising the steps of:
  (a) providing a laser which, on being fired, generates a pulse of laser-radiation;
  (b) providing a handpiece for delivering a pulse of laser-radiation from said laser to the skin being treated;
  (c) while moving the handpiece over the skin being treated, electronically determining the location of said handpiece in the area of skin being treated, wherein said location determining further compromises the steps of (i) providing a roller on the handpiece, said roller arranged to contact the skin being treated and rotate in response to the handpiece being moved over the skin being treated, and said roller having a plurality of regularly spaced indicia thereon (ii) providing at least one sensor on the handpiece said sensor arranged to detect passage by said sensor of one or more of said indicia as said roller rotates; and
  (d) automatically firing the laser when said electronically determined location corresponds to a sub-area to be treated, wherein said automatic firing is triggered by the passage by said sensor of one or more of said indicia.

13. The method of claim 12, wherein said indicia are radially extending lines on a side of said roller.

14. The method of claim 12 wherein said indicia are longitudinally extending lines on a first cylindrical surface of said roller.

15. The method of claim 14, wherein said indicia are spaced apart at the periphery of said roller by a distance equal to one of a linear dimension of the sub-area irradiated by said laser pulse; a distance equal to a sub-multiple of a linear dimension of the sub-area irradiated by said laser pulse; and a distance relatively small compared with a linear dimension of the sub-area irradiated by said laser pulse.

16. The method of claim 14 wherein said first cylindrical surface of said roller is a skin contacting surface of said roller.

17. The method of claim 14 wherein said roller has a second cylindrical surface for contacting the skin, and first cylindrical surface has a smaller diameter than the diameter of said second cylindrical surface.

18. A method of treating an area of skin with a laser by delivering a series of laser-radiation pulses to the skin, each of the laser pulses treating a sub-area of the area to be treated, the method comprising the steps of:
  (a) providing a laser which, on being fired, generates a pulse of laser-radiation;
  (b) providing a handpiece for delivering a pulse of laser-radiation from said laser to the skin being treated;
  (c) while moving the handpiece over the skin being treated, electronically determining the location of said handpiece in the area of skin being treated, wherein said location determining further comprising the step of providing a roller on the handpiece, said roller arranged to contact the skin being treated and rotate in response to the handpiece being moved over the skin being treated said roller being axially connected to a shaft encoder said shaft encoder providing signals used for said electronic location determining; and
  (d) automatically firing the laser when said electronically determined location corresponds to a sub-area to be treated.

19. A method of treating an area of skin with a laser by delivering a series of laser-radiation pulses to the skin, each of the laser pulses treating a sub-area of the area to be treated, the method comprising the steps of:
  (a) providing a laser which, on being fired, generates a pulse of laser-radiation;
  (b) providing a handpiece for delivering a pulse of laser-radiation from said laser to the skin being treated;
  (c) while moving the handpiece over the skin being treated, electronically determining the location of said handpiece in the area of skin being treated wherein said location determining further comprises the steps of (i) providing a screen adjacent the skin being treated (ii) providing a transponder on the handpiece, said transponder arranged to emit a regular train of signal-pulses toward said screen such that said signal-pulses are incident thereon and a return-pulse corresponding to each of said incident signal-pulses returns to the handpiece (iii) providing a receiver on said handpiece for receiving said return pulses (iv) determining an elapsed time between emitting a said signal-pulse and receiving a said corresponding return-pulse, said elapsed time being representative of said location of said handpiece; and
  (d) automatically firing the laser when said electronically determined location corresponds to a sub-area to be treated.

20. The method of claim 19 wherein said signal-pulses are ultrasonic pulses.

21. The method of claim 19 wherein said signal-pulses are optical pulses.

22. The method of claim 19 wherein said signal-pulses are radar pulses.

23. A method of treating an area of skin with a laser by delivering a series of laser-radiation pulses to the skin, each of the laser pulses treating a sub-area of the area to be treated, the method comprising the steps of:
  (a) providing a laser which, on being fired, generates a pulse of laser-radiation;
  (b) providing a handpiece for delivering a pulse of laser-radiation from said laser to the skin being treated;
  (c) while moving the handpiece over the skin being treated, electronically determining the location of said handpiece in the area of skin being treated wherein said location determining further comprises the steps of (i) providing a transponder on the handpiece, said transponder arranged to emit a regular train of signal-pulses each thereof in diverging beam (ii) providing at least two spaced-apart receivers located in a position remote from said handpiece, within the divergence of said beam, for receiving said signal pulses (iii) based on the spacing of said receivers and an arrival time of said signal pulses at said receivers determining said location of said handpiece in at least length and width dimensions of said area of skin to be treated; and (d) automatically firing the laser when said electronically determined location corresponds to a sub-area to be treated.

24. The method of claim 23, wherein said area of skin to be treated is contoured and said two spaced apart receivers are provided, and said location of said handpiece in said area of skin to be treated is determined in length, width and height dimensions.

25. The method of claim 23 wherein said signal-pulses are one of ultrasonic pulses, optical pulses, or radar pulses.

26. The method of claim 25 wherein said signal pulses are ultrasonic pulses.

27. A method of treating an area of skin with a laser by delivering a series of laser-radiation pulses to the skin, each of the laser pulses treating a sub-area of the area to be treated, the method comprising the steps of:

(a) providing a laser which, on being fired, generates a pulse of laser-radiation;

(b) providing a handpiece for delivering a pulse of laser-radiation from said laser to the skin being treated;

(c) while moving the handpiece over the skin being treated, electronically determining s location of said handpiece in the area of skin being treated said location determining including (i) providing a plurality of regularly spaced indicia on or adjacent the area of skin being treated, and (ii) providing at least one sensor on the handpiece said sensor arranged to detect passage of the handpiece by one or more of said indicia as the handpiece is moved over the skin being treated; and (d) automatically firing the laser on detection of passage of the handpiece by one or more of said indicia.

28. A method of treating an area of skin with a laser by delivering a series of laser-radiation pulses to the skin, each of the laser pulses treating a sub-area of the area to be treated, the method comprising the steps of:

(a) providing a laser which, on being fired, generates a pulse of laser-radiation;

(b) providing a handpiece for delivering a pulse of laser-radiation from said laser to the skin being treated;

(c) while moving the handpiece over the skin being treated, electronically determining a location of said handpiece in the area of skin being treated said location determining including (i) providing a roller on the handpiece, said roller arranged to contact the skin being treated and rotate in response to the handpiece being moved over the skin being treated, and said roller having a plurality of regularly spaced indicia thereon and (ii) providing at least one sensor on the handpiece, said sensor arranged to detect passage by said sensor of one or more of said indicia as said roller rotates; and (d) automatically firing the laser on detection of passage by the sensor of one of more of said indicia.

29. The method of claim 28, wherein said indicia are radially-extending lines on a side of said roller.

30. A method of treating an area of skin with a laser by delivering a series of laser-radiation pulses to the skin, each of the laser pulses treating a sub-area of the area to be treated, the method comprising the steps of:

(a) providing a laser which, on being fired, generates a pulse of laser-radiation;

(b) providing a handpiece for delivering a pulse of lasr-radiation from said laser to the skin being treated;

(c) while moving the handpiece over the skin being treated, electronically determining a location of said handpiece in the area of skin being treated said location determining including (i) providing a screen adjacent the skin being treated, (ii) providing a transponder on the handpiece, said transponder arranged to emit a regular train of signal-pulses toward said screen such that said signal-pulses are incident thereon and a return-pulse corresponding to each of said incident signal-pulses returns to the handpiece, (iii) providing a receiver on said handpiece for receiving said return pulses, and (iv) determining an elapsed time between emitting a said signal-pulse and receiving a said corresponding return-pulse, said elapsed time being representative of said location of said handpiece; and (d) automatically firing the laser when said electronically determined location corresponds to a sub-area to be treated.

31. A method of treating an area of skin with a laser by delivering a series of laser-radiation pulses to the skin, each of the laser pulses treating a sub-area of the area to be treated, the method comprising the steps of:

(a) providing a laser which, on being fired, generates a pulse of laser-radiation;

(b) providing a handpiece for delivering a pulse of laser-radiation from said laser to the skin being treated;

(c) while moving the handpiece over the skin being treated, electronically determining a location of said handpiece in the area of skin being treated said location determining including (i) providing a transponder on the handpiece, said transponder arranged to emit a regular train of signal-pulses each thereof in diverging beam, (ii) providing at least two spaced-apart receivers located in a position remote from said handpiece, within the divergence of said beam, for receiving said signal pulses, and (iii) based on the spacing of said receivers and an arrival time of said signal pulses at said receivers determining said location of said handpiece in at least length and width dimensions of said area of skin to be treated; and (d) automatically firing the laser when said electronically determined location corresponds to a sub-area to be treated.

32. The method of claim 31, wherein said area of skin to be treated is contoured and three spaced-apart receivers are provided, and said location of said handpiece in said area of skin to be treated is determined in length width and height dimensions.

33. A laser system for treating tissue comprising:

a laser for generating laser light;

a delivery device including a manually movable handpiece for delivering the laser light to the tissue;

a ruled indicia spatially associated with the tissue to be treated;

a sensor associated with said handpiece, said sensor being adapted to detect said indicia as said handpiece is moved, thereby monitoring the movement of said handpiece with respect to the tissue, said sensor generating output signals; and a processor for controlling the triggering of said laser in response to the receipt of said output signals in a manner to facilitate uniform treatment of said tissue over an area with said laser light.

34. A laser system as recited in claim 33 wherein said indicia are formed by one of:
   a) markings directly on the tissue to be treated; and
   b) markings on a rule located proximate the surface of the skin.

35. A laser system is as recited in claim 34 wherein said indicia are graphic and said sensor detects the indicia optically.

36. A laser system as recited in claim 35 wherein said sensor includes a light source aimed at said indicia, said sensor further including a photodetector configured to monitor changes in light caused by the presence of the indicia.

37. A laser system for treating tissue comprising:
   a laser for generating laser light;
   a delivery device including a manually movable handpiece for delivering the laser light to the tissue;
   a sensor associated with the handpiece wherein said sensor includes a wheel rotatably mounted to the handpiece, said wheel being adapted to rotate in response to the movement of said handpiece across the tissue, and said sensor adapted to monitor the rotation of the wheel, said sensor being further adapted to generate output signals; and
   a processor for controlling the triggering of said laser in response to the receipt of said output signals in a manner to facilitate uniform treatment of said tissue over an area with said laser light.

38. A laser system as recited in claim 37 wherein the wheel includes ruled indicia which are monitored by the sensor.

* * * * *